(12) United States Patent
Matheny

(10) Patent No.: US 12,343,254 B2
(45) Date of Patent: *Jul. 1, 2025

(54) PROSTHETIC HEART VALVES

(71) Applicant: CorMatrix Cardiovascular, Inc., Roswell, GA (US)

(72) Inventor: Robert G Matheny, Norcross, GA (US)

(73) Assignee: Corvivo Cardiovascular, Inc., Gainesville, FL (US)

(*) Notice: Subject to any disclaimer, the term of this patent is extended or adjusted under 35 U.S.C. 154(b) by 1068 days.

This patent is subject to a terminal disclaimer.

(21) Appl. No.: 17/233,890

(22) Filed: Apr. 19, 2021

(65) Prior Publication Data

US 2021/0236277 A1 Aug. 5, 2021

Related U.S. Application Data

(63) Continuation-in-part of application No. 17/177,359, filed on Feb. 17, 2021, now Pat. No. 12,053,372, and (Continued)

(51) Int. Cl.
*A61F 2/24* (2006.01)
*A61L 27/24* (2006.01)
(Continued)

(52) U.S. Cl.
CPC .......... *A61F 2/2418* (2013.01); *A61F 2/2412* (2013.01); *A61L 27/24* (2013.01); (Continued)

(58) Field of Classification Search
CPC ............ A61F 2/2418; A61F 2220/0008; A61F 2/2412; A61L 17/06; A61L 27/3625; (Continued)

(56) References Cited

U.S. PATENT DOCUMENTS 6,117,979 A 9/2000 Hendriks et al.
9,446,078 B2 * 9/2016 Matheny ............ A61K 38/2086
(Continued)

FOREIGN PATENT DOCUMENTS

WO 2014/133539 A1 9/2014
WO 2016/050751 A1 4/2016

OTHER PUBLICATIONS

Extended Search Report, EP Application No. 24153745.5, mailed Apr. 16, 2024.
(Continued)

*Primary Examiner* — Suba Ganesan
(74) *Attorney, Agent, or Firm* — Thomas | Horstemeyer, LLP

(57) ABSTRACT

Prosthetic heart valves having a conical shaped base valve structure formed from collagenous mammalian tissue and an expandable stent structure. The base valve structure includes a plurality of elongated ribbon members that are positioned proximate each other in a joined relationship, wherein the elongated ribbon members are positioned adjacent each other and form a plurality of fluid flow modulating regions that open when fluid into and through the base valve structure exhibits a positive pressure relative to the exterior pressure, i.e., a positive pressure differential, wherein the fluid is allowed to be transmitted out of the base valve structure, and transition to a closed configuration when the pressure differential between the interior valve pressure and exterior pressure reduces, wherein the fluid is restricted from flowing out of the base valve structure. The expandable stent structure includes a plurality of tethers adapted to pierce
(Continued)

cardiovascular tissue and, thereby, position the base valve structure and, thereby, prosthetic valves formed therewith on said heart valve annulus.

17 Claims, 15 Drawing Sheets

Related U.S. Application Data a continuation-in-part of application No. 16/129,968, filed on Sep. 13, 2018, now Pat. No. 10,952,843, which is a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61L 27/36* (2006.01)
*A61L 27/38* (2006.01)

(52) U.S. Cl.
CPC ....... *A61L 27/3625* (2013.01); *A61L 27/3629* (2013.01); *A61L 27/3641* (2013.01); *A61L 27/3687* (2013.01); *A61L 27/3834* (2013.01); *A61F 2/2457* (2013.01); *A61F 2220/0008* (2013.01); *A61L 2300/222* (2013.01); *A61L 2300/426* (2013.01); *A61L 2400/16* (2013.01); *A61L 2430/20* (2013.01)

(58) Field of Classification Search
CPC ............. A61L 27/3641; A61L 27/3687; A61L 27/3834; A61L 2400/16; A61L 2430/20
See application file for complete search history.

(56) References Cited

U.S. PATENT DOCUMENTS

| | | |
|---|---|---|
| 2013/0190860 A1 | 7/2013 | Sundt, III |
| 2014/0330369 A1 | 11/2014 | Matheny |
| 2016/0317300 A1 | 11/2016 | Matheny |
| 2017/0100512 A1* | 4/2017 | Matheny ................. A61L 27/34 |
| 2018/0104050 A1* | 4/2018 | Matheny ............... A61F 2/2412 |
| 2018/0153686 A1 | 6/2018 | Matheny |
| 2020/0022808 A1* | 1/2020 | Matheny ............... A61F 2/2412 |
| 2020/0069840 A1 | 3/2020 | Matheny |
| 2020/0368178 A1 | 11/2020 | Naso et al. |

OTHER PUBLICATIONS

Search Report mailed on Oct. 16, 2024 for European Patent Application No. 21926982.6. (Copy Provided).
Search Report mailed on Oct. 17, 2024 for European Patent Application No. 21926977.6. (Copy Provided).
Search Report mailed on Oct. 16, 2024 for European Patent Application No. 21926991.7. (Copy Provided).

* cited by examiner

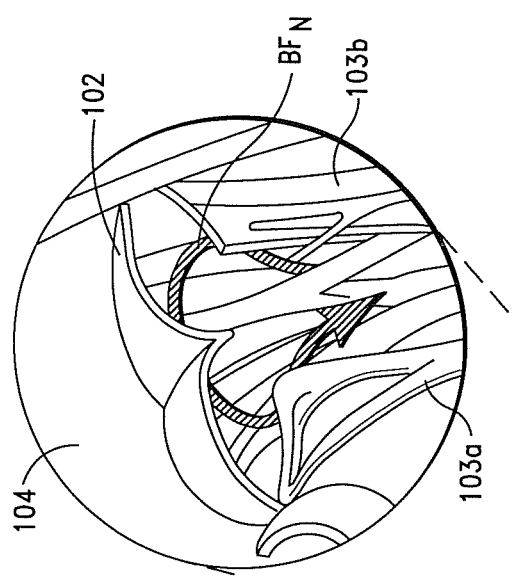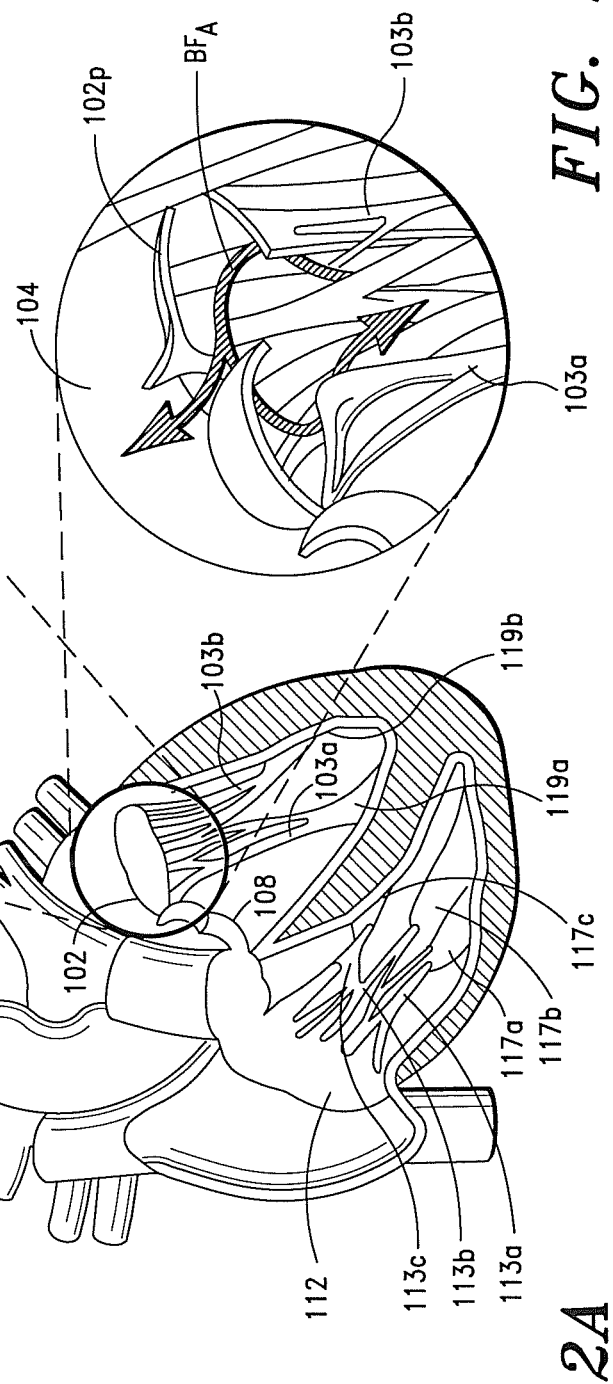

PROSTHETIC HEART VALVES

CROSS-REFERENCE TO RELATED APPLICATIONS

This application is a continuation-in-part of U.S. application Ser. No. 17/177,359, filed on Feb. 17, 2021, which is a continuation-in-part of U.S. application Ser. No. 16/129,968, filed on Sep. 13, 2018, now U.S. Pat. No. 10,952,843, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic heart valves for replacing diseased or defective heart valves. More particularly, the present invention relates to improved prosthetic heart valves and methods for replacing native heart valves with same.

BACKGROUND OF THE INVENTION

As is well known in the art, the human heart has four heart valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIG. 2A, there are also generally five papillary muscles in the heart 100. The anterior, posterior and septal papillary muscles 117a, 117b, 117c, which are in the right ventricle 116, attach via chordae tendineae 113a, 113b, 113c to the tricuspid valve 112. The anterior and posterior papillary muscles 119a, 119b, which are in the left ventricle 106, attach via chordae tendineae 103a, 103b to the mitral valve 102.

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordae or several disease states. Stenosis and insufficiency can also occur concomitantly in the same valve or in different valves.

Both of the noted valve abnormalities can adversely affect organ function and result in heart failure. By way of example, referring first to FIG. 2B, there is shown normal blood flow (denoted "$BF_N$") proximate the mitral valve 102 during closure.

Referring now to FIG. 2C, there is shown abnormal blood flow (denoted "$BF_A$") or regurgitation caused by a prolapsed mitral valve 102p. As illustrated in FIG. 2C, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e., "vegetation") on the valve leaflets. The vegetation can, and in many instances will, flake off (i.e., "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e., a prosthetic valve.

Various prosthetic heart valves have thus been developed for replacement of native diseased or defective heart valves. The selection of a particular type of replacement valve depends on many factors, such as the location of the diseased or defective native valve, the age and other specifics of the recipient of the replacement heart valve, and the surgeon's experiences and preferences.

Commonly used replacement heart valves are typically classified in the following three groups: (i) mechanical valves, (ii) allograft tissue valves, and (iii) xenograft tissue valves. Each of the noted valves and disadvantages associated with same are discussed in detail below.

Mechanical Heart Valves

As is well known in the art, mechanical heart valves, such as caged-ball valves, bi-leaflet valves, and tilting disk valves, typically comprise various metal and polymeric components, which can, and in most instances will, induce an adverse inflammatory response when implanted in a patient or subject.

A further disadvantage associated with mechanical heart valves is that such valves also have a propensity to cause the formation of blood clots after implantation in a patient. If such blood clots form on the mechanical valve, they can preclude the valve from opening or closing correctly or, more importantly, can disengage from the valve and embolize to the brain, causing an embolic stroke. Thus, recipients of a mechanical heart valve are typically required to take systemic anticoagulant drugs for the rest of their lives. In addition to being expensive, these anticoagulant drugs can themselves be dangerous in that they can cause abnormal bleeding in the recipient or patient that can lead to a hemorrhagic stroke.

A further disadvantage associated with mechanical heart valves is that such valves are notoriously difficult to implant and often require large and cumbersome catheter assemblies for percutaneous or transapical implantation. These large catheter assemblies are excessively difficult to operate during a percutaneous or transapical implantation procedure.

Allograft Tissue Valves

As is also well known in the art, allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major disadvantage associated with allograft tissue valves is that such valves are not available in sufficient numbers to satisfy the needs of all patients who need new heart valves.

A further major disadvantage associated with allograft tissue valves is that recipients of allograft tissue valves, i.e., patients, are typically required to take systemic antirejection and/or immunosuppressive drugs for a predetermined period of time and, in some instances, for a lifetime. Although antirejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Xenograft Tissue Valves

As is additionally well known in the art, xenograft tissue valves are formed from non-human tissue sources, such as cows or pigs. Xenograft tissue valves are similarly less likely to cause blood clot formation than comparable mechanical valves. However, there are also several drawbacks and disadvantages associated with most conventional allograft tissue valves.

A major disadvantage associated with conventional xenograft tissue valves is that such valves often comprise glutaraldehyde processed tissue and, hence, are prone to calcification and lack the long-term durability of mechanical valves.

More recently, remodelable xenograft tissue valves comprising decellularized extracellular matrix (ECM) have been developed and employed to replace native diseased or defective heart valves. Such valves are not prone to calcification and, as set forth in Applicant's U.S. Pat. Nos. 9,308,084, 9,011,526, 8,709,076 and 10,952,843, which are expressly incorporated by reference herein in their entirety, have the capacity to remodel, i.e., form valve structures similar to native valve structures when implanted in a patient, and induce remodeling of native cardiovascular tissue and regeneration of new cardiovascular tissue when implanted in a patient.

Although most remodelable xenograft ECM tissue valves substantially reduce and, in most instances, eliminate the major disadvantages and drawbacks associated with mechanical valves, allograft tissue valves, and conventional xenograft tissue valves, a remaining disadvantage associated with xenograft tissue valves (non-remodelable and remodelable) is that secure, sealed engagement of such valves to valve annuli can be, and many times is, difficult to achieve.

A further disadvantage associated with xenograft tissue valves is that such valves similarly often require complex stent structures to provide acceptable structural integrity. Although most of the stent structures do provide acceptable structural integrity, the stent structures often result in complex implant procedures to properly position the associated valves in valve annuli and sealed engagement thereto.

There is thus a need for xenograft tissue valve stent structures that provide acceptable structural integrity and facilitate percutaneous valve implant procedures to position prosthetic xenograft tissue valves formed therewith in valve annuli.

There is also a need for xenograft tissue valve stent structures that provide acceptable structural integrity and facilitate secure, sealed engagement of prosthetic xenograft tissue valves formed therewith via percutaneous valve implant procedures.

It is therefore an object of the present invention to provide xenograft tissue valve stent structures that provide acceptable structural integrity and facilitate percutaneous valve implant procedures to position prosthetic xenograft tissue valves formed therewith in valve annuli.

It is another object of the present invention to provide xenograft tissue valve stent structures that provide acceptable structural integrity and facilitate secure, sealed engagement of prosthetic xenograft tissue valves formed therewith via percutaneous valve implant procedures.

It is yet another object of the present invention to provide improved methods for replacing diseased or defective native heart valves with prosthetic xenograft tissue valves.

SUMMARY OF THE INVENTION

The present invention is directed to prosthetic valves that can be readily employed to replace diseased or defective native heart valves.

In a preferred embodiment of the invention, the prosthetic valves comprise a base valve structure and an expandable stent structure.

In a preferred embodiment, the base valve structures comprise continuous conical shaped structural members comprising a plurality of flow modulation means.

In some embodiments of the invention, the conical shaped structural members comprise conical shaped ribbon structures comprising a plurality of elongated ribbon members.

In a preferred embodiment of the invention, the edge regions of the elongated ribbon members are positioned proximate each other and form the fluid flow modulating means.

In a preferred embodiment of the invention, the distal ends of the elongated ribbon members are in a joined relationship, wherein fluid flow through the joined distal ends of the elongated ribbon members is restricted.

In some embodiments of the invention, the conical shaped structural members comprise conical shaped sheet structures.

In the noted embodiments, the flow modulation means comprise linear interstices.

In a preferred embodiment of the invention, the base valve structures comprise collagenous mammalian tissue derived from a mammalian tissue source.

In some embodiments of the invention, the collagenous mammalian tissue comprises pericardium tissue.

In some embodiments of the invention, the pericardium tissue comprises crosslinked pericardium tissue.

In some embodiments of the invention, the collagenous mammalian tissue comprises at least one additional biologically active agent or composition, i.e., an agent that induces or modulates a physiological or biological process, or cellular activity, and/or at least one pharmacological agent or composition (or drug), i.e., an agent or composition that is capable of producing a desired biological effect in vivo, such as stimulation or suppression of apoptosis, stimulation or suppression of an immune response, etc.

In a preferred embodiment of the invention, the stent structure is configured and adapted to enhance the structural integrity of the base valve structures and, hence, prosthetic valves of the invention.

In a preferred embodiment of the invention, the stent structure comprises a plurality of tethers that are configured and adapted to position the base valve structures and, hence, prosthetic valves of the invention at a desired valve annulus region and, in some embodiments, secure the prosthetic valves thereto.

In a preferred embodiment, the stent structure comprises a shape-memory, surgical-grade alloy.

In a preferred embodiment, the shape-memory alloy comprises a nickel-titanium alloy (referred to herein as "Nitinol®").

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 2A is a further schematic illustration of a human heart;

FIG. 2B is an illustration of a normal mitral valve;

FIG. 2C is an illustration of a prolapsed mitral valve;

DETAILED DESCRIPTION OF THE PREFERRED EMBODIMENT

Figure 1A:
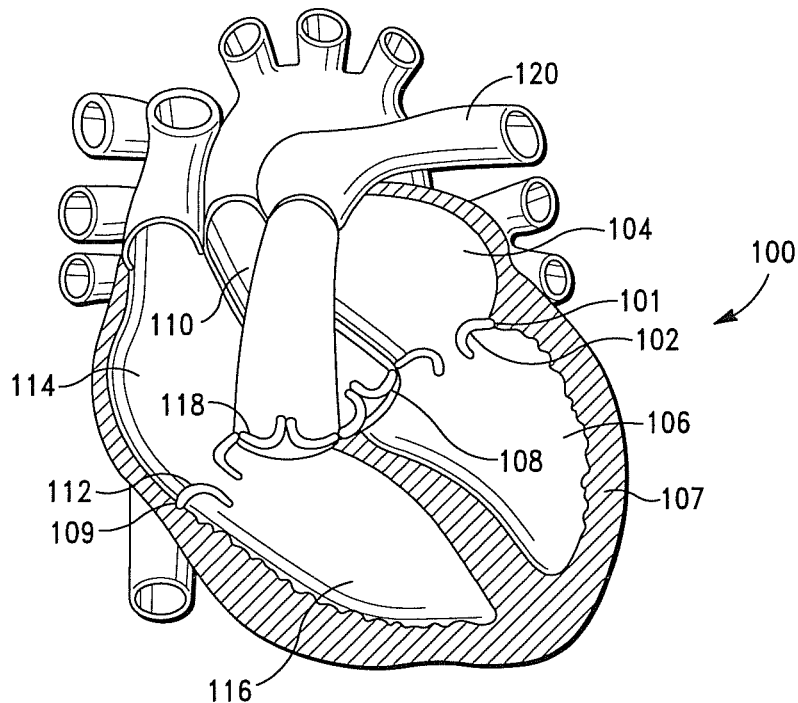
FIGS. 1A and 1B are schematic illustrations of a human heart.
Figure 1B:
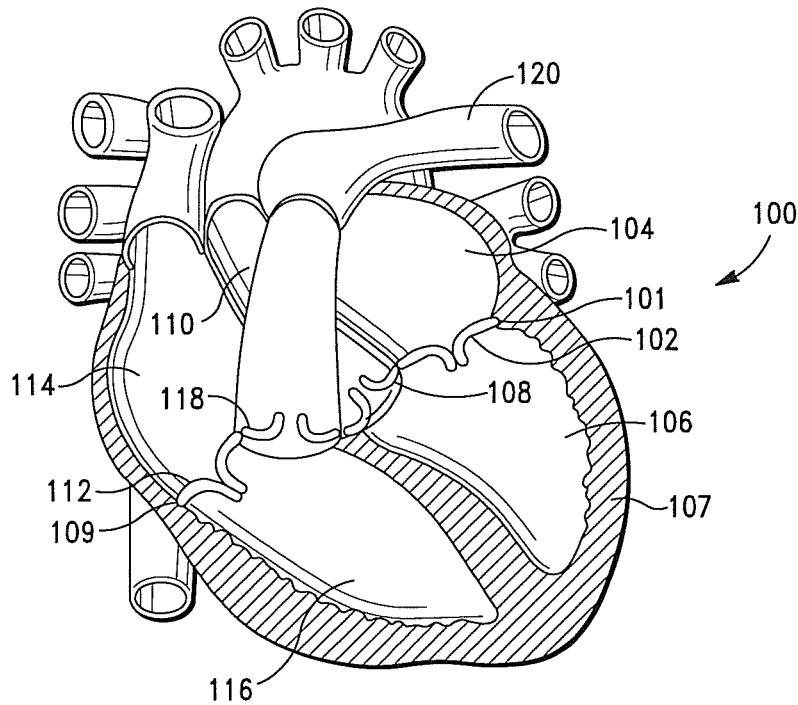

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed.

It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means ECM that has a reduced content of cells.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM can also comprise collagen from mammalian sources.

The terms "heart tissue" and "cardiac tissue" are used collectively herein, and mean and include, without limitation, mammalian tissue derived from any cardiovascular structure including, without limitation, pericardial tissue, myocardial tissue, vascular tissue and the like.

The terms "collagenous mammalian tissue" and "collagenous tissue" are used collectively herein, and mean and include, without limitation, tissue that is also derived from a mammalian tissue source.

According to the invention, the collagenous mammalian tissue can similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

The collagenous mammalian tissue can also be derived from a mammalian tissue source that is devoid of xenogeneic antigens, including, without limitation, collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetylneuraminic acid hydroxylase, swine leukocyte antigen class I and porcine endogenous retrovirus polymerase (referred to herein as "immune privileged collagenous mammalian tissue").

The term "genetically modified organism", as used herein means and includes any living organism that has at least one gene modified by artificial means, e.g., gene editing.

The term "immune privileged collagenous mammalian tissue", as used herein means and includes xenogeneic collagenous mammalian tissue that can be disposed proximate mammalian tissue with a minimal or virtually absent adverse immune response; particularly, an adverse immune response associated with xenogeneic tissue graft rejection.

According to the invention, the term "mammalian" means and includes, without limitation, warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "crosslinked collagenous mammalian tissue", as used herein, means and includes mammalian tissue that exhibits at least 25% chemical bonding of adjacent chains of molecules, i.e., collagen fibrils, which comprise the collagenous mammalian tissue.

The term "polymer", as used herein means and includes, without limitation, polyurethane urea, porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™) and polyethylene terephthalate (Dacron™).

The term "biologically active agent", as used herein, means and includes an agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β) and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatoiren-steroidal anti-inflammatoirenti-neoplastics, anti-spasmodics, modulators of cell-extracellular matrix interactions, proteins, hormones, growth factors, matrix metalloproteinases (MMPs), enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the Class I-Class V antiarrhythmic agents disclosed in Applicant's U.S. Pat. Nos. 9,119,841, 10,188,509, 10,188,510, 10,143,778 and 10,952,843, and Co-pending application Ser. No. 16/990,236, including, without limitation, (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the antibiotics disclosed in Applicant's U.S. Pat. Nos. 9,119,841, 10,188,509, 10,188,510, 10,143,778 and 10,952,843, and Co-pending application Ser. No. 16/990,236, including, without limitation, aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

The terms "anti-inflammatory" and "anti-inflammatory agent" thus include the anti-inflammatoires disclosed in Applicant's U.S. Pat. Nos. 9,119,841, 10,188,509, 10,188,510, 10,143,778 and 10,952,843, and Co-pending application Ser. No. 16/990,236, including, without limitation, desoximetasone, dexamethasone dipropionate, cloticasone propionate, diftalone, fluorometholone acetate, fluquazone, meseclazone, mesterolone, methandrostenolone, methenolone, methenolone acetate, methylprednisolone suleptanate, halopredone acetate, alclometasone dipropionate, apazone, balsalazide disodium, cintazone cormethasone acetate, cortodoxone, diflorasone diacetate, diflumidone sodium, endrysone, fenpipalone, flazalone, fluretofen, fluticasone propionate, isoflupredone acetate, nabumetone, nandrolone, nimazone, oxyphenbutazone, oxymetholone, phenbutazone, pirfenidone, prifelone, proquazone, rimexolone, seclazone, tebufelone and testosterone.

The terms "pharmacological agent", "active agent" and "drug" also mean and include the statins, i.e., HMG-COA reductase inhibitors, disclosed in Applicant's U.S. Pat. Nos. 9,119,841, 10,188,509, 10,188,510, 10,143,778 and 10,952,843, and Co-pending application Ser. No. 16/990,236, including, without limitation, atorvastatin, cerivastatin, fluvastatin and lovastatin.

The terms "pharmacological agent", "active agent", "drug" and "active agent formulation" further mean and include the anti-proliferative agents disclosed in Applicant's U.S. Pat. Nos. 9,119,841, 10,188,509, 10,188,510, 10,143,778 and 10,952,843, and Co-pending application Ser. No. 16/990,236, including, without limitation, paclitaxel, sirolimus and derivatives thereof, including everolimus.

The term "pharmacological composition", as used herein, means and includes a composition comprising a "pharmacological agent" and/or any additional agent or component identified herein.

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The term "comprise" and variations of the term, such as "comprising" and "comprises," as used in connection with the a prosthetic valve composition and/or mammalian tissue, also means a composition and/or mammalian tissue employed to form a prosthetic valve structure, such as a sheet member, and, hence, a prosthetic valve of the invention.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic valves that can be readily employed to replace diseased or defective native heart valves.

Although the prosthetic valves of the invention are described in connection with prosthetic tricuspid valves and the replacement of native tricuspid valves therewith, it is to be understood that the prosthetic valves of the invention are not limited to prosthetic tricuspid valves and the replacement of native tricuspid valves therewith. Indeed, the prosthetic valves of the invention can also be readily employed to replace other cardiovascular valves, including mitral and venous valves.

As indicated above, in a preferred embodiment of the invention, the prosthetic valves comprise a base valve structure and an internal expandable stent structure.

As also indicated above, in a preferred embodiment, the prosthetic valves of the invention comprise continuous conical shaped structural members comprising a plurality of flow modulation means.

In some embodiments of the invention, the continuous conical shaped structural members comprise conical shaped "ribbon structures" comprising a plurality of elongated ribbon members, wherein the edge regions of the elongated ribbon members are positioned proximate each other and form the fluid flow modulating means.

In a preferred embodiment of the invention, the distal ends of the elongated ribbon members are in a joined relationship, wherein fluid flow through the joined distal ends of the elongated ribbon members is restricted.

In some embodiments of the invention, the continuous conical shaped structural members comprise conical shaped "sheet structures", such as the conical shaped valves disclosed in Applicant's U.S. Pat. Nos. 10,188,509, 10,188,510 and 10,188,513, which are incorporated by reference herein in their entirety.

In the noted sheet structure embodiments, the flow modulation means comprise linear interstices.

As set forth in Applicant's Co-pending U.S. application Ser. No. 17/177,359 and Applicant's U.S. Pat. Nos. 10,188,509, 10,188,510 and 10,188,513, which are incorporated by reference herein, according to the invention, the base valve structure can comprise and, hence, be formed with various biocompatible materials and compositions.

In some embodiments of the invention, the base valve structures of the invention are formed from and, hence, comprise an ECM composition comprising acellular ECM from a mammalian tissue source.

According to the invention, suitable mammalian tissue sources, include, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

In some embodiments of the invention, the base valve structures of the invention are formed from and, hence, comprise a polymeric composition comprising at least one polymer; preferably, a biocompatible polymer.

According to the invention, suitable biocompatible polymers include, without limitation, polyurethane urea, including porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™), and polyethylene terephthalate (Dacron™).

In some embodiments, the ECM composition and/or polymeric composition further comprises at least one additional biologically active agent or composition, i.e., an agent that induces or modulates a physiological or biological process, or cellular activity, and/or at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable biologically active agents and pharmacological agents include any of the aforementioned biologically active agents, including, without limitation, the aforementioned growth factors, cells and proteins, and pharmacological agents, including, without limitation, the aforementioned antibiotics and anti-inflammatories.

In a preferred embodiment of the invention, the base valve structures of the invention are formed with and, hence, comprise pericardium tissue.

In some embodiments of the invention, the pericardium tissue is devoid of xenogeneic antigens.

In some embodiments, the pericardium tissue similarly comprises at least one additional biologically active agent or composition and/or at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable biologically active agents and pharmacological agents similarly include any of the aforementioned biologically active agents, including, without limitation, the aforementioned growth factors, cells and proteins, and pharmacological agents, including, without limitation, the aforementioned antibiotics and anti-inflammatories.

As indicated above, in a preferred embodiment of the invention, the prosthetic valves of the invention further comprise an expandable stent structure that is configured and adapted to enhance the structural integrity of the base valve structures and, hence, prosthetic valves of the invention.

As also indicated above, in a preferred embodiment, the stent structure comprises a plurality of tethers that are configured and adapted to position the base valve structures and, hence, prosthetic valves of the invention at a desired valve annulus region and, in some embodiments, secure the prosthetic valves thereto.

In a preferred embodiment of the invention, the expandable stent structure comprises a shape-memory, surgical-grade alloy.

In a preferred embodiment, the shape-memory alloy comprises a superelastic nickel-titanium (Ni—Ti) alloy (referred to hereinafter as "Nitinol®").

In some embodiments, the expandable stent structure comprises an outer coating.

In some embodiments of the invention, the outer coating comprises an immunomodulating compound.

In some embodiments, the immunomodulating compound comprises a polysaccharide, including, without limitation, GAGs, dextrans, alginate and chitosan.

In some embodiments, the immunomodulating compound comprises a polymeric material, including, without limitation, high molecular weight hyaluronic acid (HMW-HA).

In some embodiments, the outer coating comprises one of the aforementioned ECM or polymeric compositions.

In some embodiments of the invention, the ECM composition comprises an expandable construct, such as disclosed in Applicant's U.S. application Ser. No. 15/835,714, now U.S. Pat. No. 10,993,802, which is incorporated by reference herein.

In some embodiments of the invention, it is thus contemplated that, following placement of a prosthetic valve of the invention on or in a cardiovascular structure (or structures), such as a valve annulus, of a subject and, hence, cardiovascular tissue associated therewith, the prosthetic valve will induce "modulated healing" of the cardiovascular structure(s).

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect.

Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, a prosthetic valve of the invention is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of a prosthetic valve of the invention to restrict the expression of inflammatory components.

By way of example, according to the invention, when a base valve structure of a prosthetic valve of the invention comprises an immune privileged collagenous mammalian tissue, as defined herein, and the prosthetic valve is positioned proximate damaged tissue, the prosthetic valve will not induce an adverse immune response; particularly, an immune response associated with tissue prosthesis rejection in vivo.

In some embodiments of the invention, "modulated healing" means and includes the ability of a prosthetic valve of the invention to alter a substantial inflammatory phase (e.g., platelet or fibrin deposition) at the beginning of the tissue healing process. As used herein, the phrase "alter a substantial inflammatory phase" refers to the ability of a prosthetic valve of the invention to substantially reduce the inflammatory response at a damaged tissue site, e.g., cardiovascular vessel, when in contact with tissue at the site.

In some embodiments of the invention, such as when the base valve structure comprises an ECM composition, the term "modulated healing" also refers to the ability of a prosthetic valve formed therewith to induce host tissue proliferation, bioremodeling, including neovascularization, e.g., vasculogenesis, angiogenesis, and intussusception, and regeneration of new tissue and tissue structures with site-specific structural and functional properties, when disposed proximate damaged tissue.

Figure 3A:
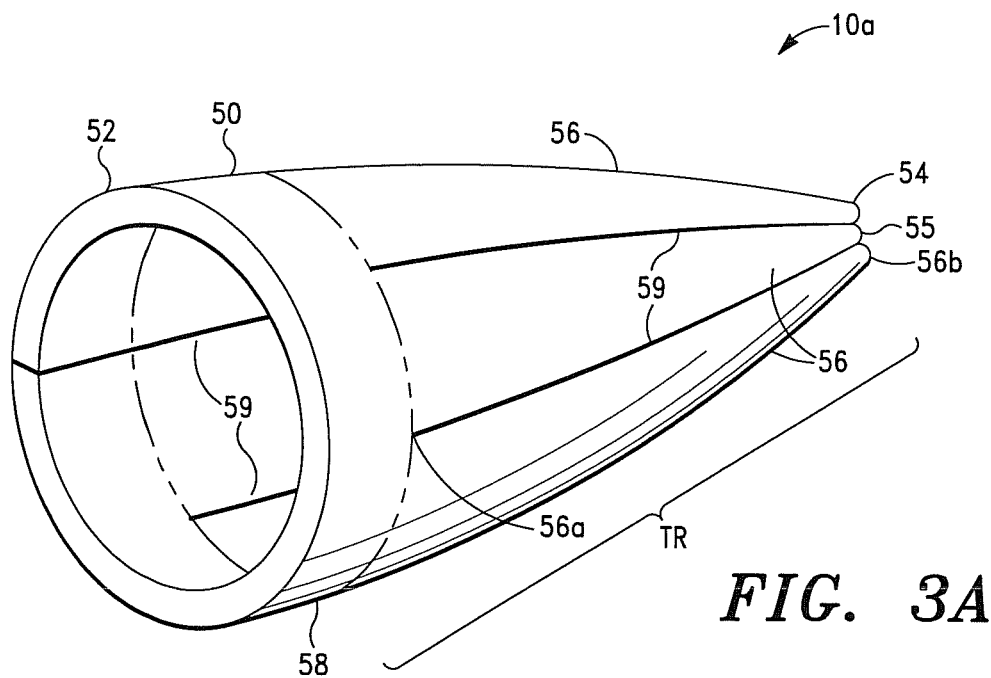
FIG. 3A is a perspective view of one embodiment of a base "ribbon structure" valve structure, in accordance with the invention.
Figure 3B:
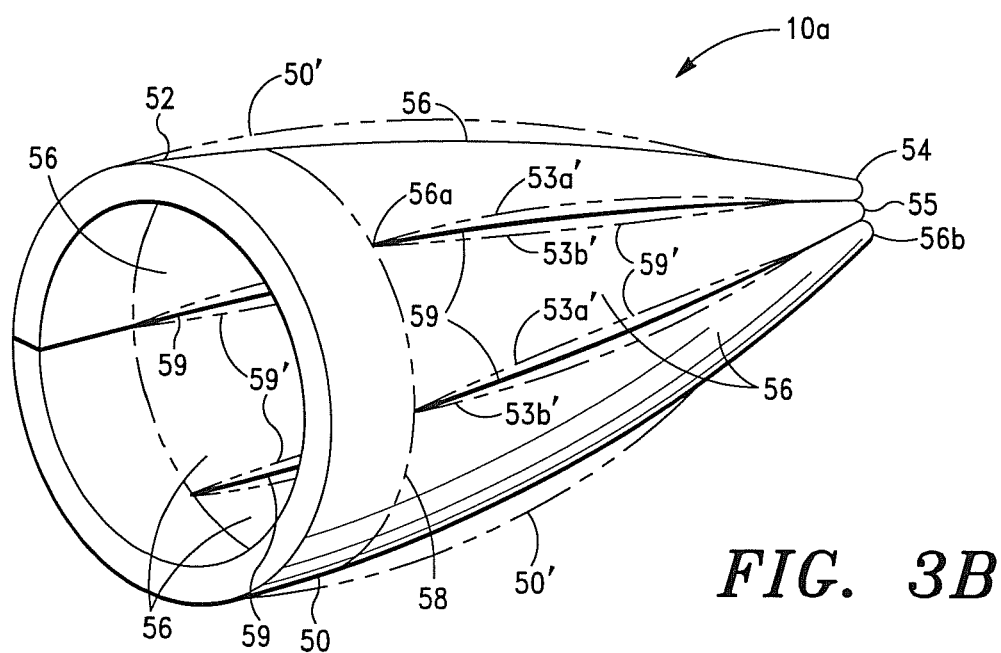
FIG. 3B is a further perspective view of the base "ribbon structure" valve structure shown in FIG. 3A, in accordance with the invention.
Figure 3C:
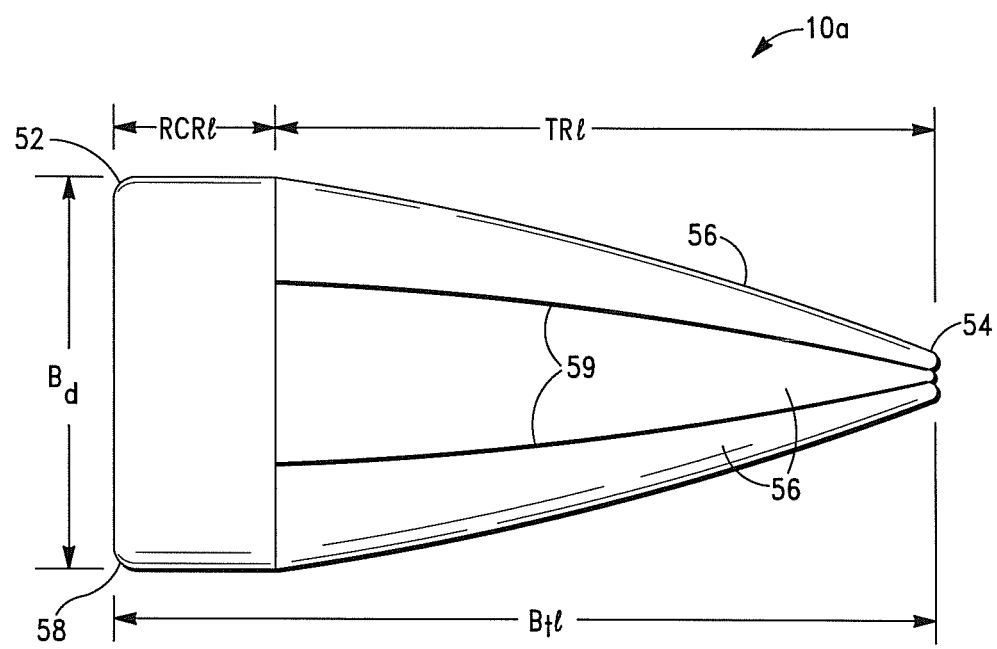
FIG. 3C is a side plan view of the base "ribbon structure" valve structure shown in FIG. 3A, in accordance with the invention.

Referring now to FIGS. 3A-3C, there is shown one embodiment of a base valve structure of the invention, denoted 10a.

As set forth in Applicant's U.S. Pat. Nos. 10,188,509 and 10,188,510, and illustrated in FIGS. 3A and 3B, the base valve structure 10a comprises a ribbon structure comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 3A and 3B, each of the plurality of ribbons 56 preferably comprise proximal and distal ends 56a, 56b, and first and second edge regions 53a, 53b that extend from the circumferential ribbon connection region 58 to the distal ends 56b of each of the ribbons 56 and, hence, distal end 54 of the base member 50.

The distal ends 56b of the ribbons 56 are also in a joined relationship, wherein blood flow through the joined distal ends 56b of the ribbons 56 is restricted.

As further illustrated in FIG. 3B, the proximal ends 56a of ribbons 56 are positioned circumferentially about the circumferential ribbon connection region 58 of the base member 50, wherein the first edge regions 53a and the second edge regions 53b of the ribbons 56 are positioned adjacent each other and form a plurality of fluid flow modulating regions 59.

As also set forth in Applicant's U.S. Pat. Nos. 10,188,510 and 10,188,509 and illustrated in FIG. 3B, when the base member 50 is engaged to a valve annulus, such as a tricuspid valve annulus, and receives blood therein that exhibits a first positive fluid pressure, whereby there is a first positive pressure differential between first internal valvular pressure (resulting from the first positive fluid pressure) and first external pressure, whereby internal forces are exerted on the internal surface of the base member 50, i.e., taper region thereof (denoted "TR" in FIG. 3A) and, thus, flow modulating regions 59, the base member 50 is adapted to expand to an expanded configuration, whereby the flow modulating regions 59 (i.e., ribbons 56) deflect outwardly to an open or unrestricted fluid flow configuration, as shown in phantom and denoted 50', i.e., the first and second edge regions 53a, 53b separate, as shown in phantom and denoted 53a', 53b', whereby the blood is allowed to be transmitted through and out of the flow modulating regions 59 and, hence, base member 50.

As further set forth in Applicant's U.S. Pat. Nos. 10,188,510 and 10,188,509 and illustrated in FIG. 3B, the base member 50 is adapted to transition from the expanded configuration to a contracted configuration, whereby the ribbons 56 deflect inwardly and the flow modulating regions 59 transition from the open fluid flow configuration to a closed or restricted fluid flow configuration during transition of the first positive pressure differential to a second pressure differential between second internal valvular pressure and second external or left ventricle pressure, the second pressure differential being lower than the first positive pressure differential, such as when blood within the base member 50 exhibits a second positive fluid pressure that is less than the first positive fluid pressure, i.e., a reduced positive fluid pressure, or a negative fluid pressure, wherein the blood through and out of the flow modulating regions 59 and, hence, base member 50 is restricted.

According to the invention, the base valve structure 10a shown in FIGS. 3A-3C and described above can be employed to construct prosthetic atrioventricular (AV)

valves of the invention, including, without limitation, prosthetic "mitral" tissue valves and prosthetic "tricuspid" tissue valves.

As will readily be appreciated by one skilled in the art, the dimensions of the prosthetic AV valves are dependent on various factors, such as the specific application, and the gender, age and cardiac pathologies of the subject.

Referring now to FIG. 3C, for purposes of describing the dimensional relationships by and between the base valve structure 10a and internal stent structures of the invention, which are described in detail below, the seminal dimensions of the base valve structure 10a are defined as follows:

$B_v l$ represents the total length of the base valve structure 10a;

TRl represents the length of the taper region (TR) of the base valve structure 10a;

RCRl represents the length of the circumferential ribbon connection region (58) of the base valve structure 10a; and $B_d$ represents the operative diameter of the proximal valve annulus engagement end (52) of the base valve structure 10a.

According to the invention, to facilitate engagement of the stent structures of the invention to the base valve structure 10a, in some embodiments, the base valve structure 10a comprises an extended circumferential ribbon connection region 58 and, thereby, an extended valve structure length ($B_v l$).

Figure 4A:
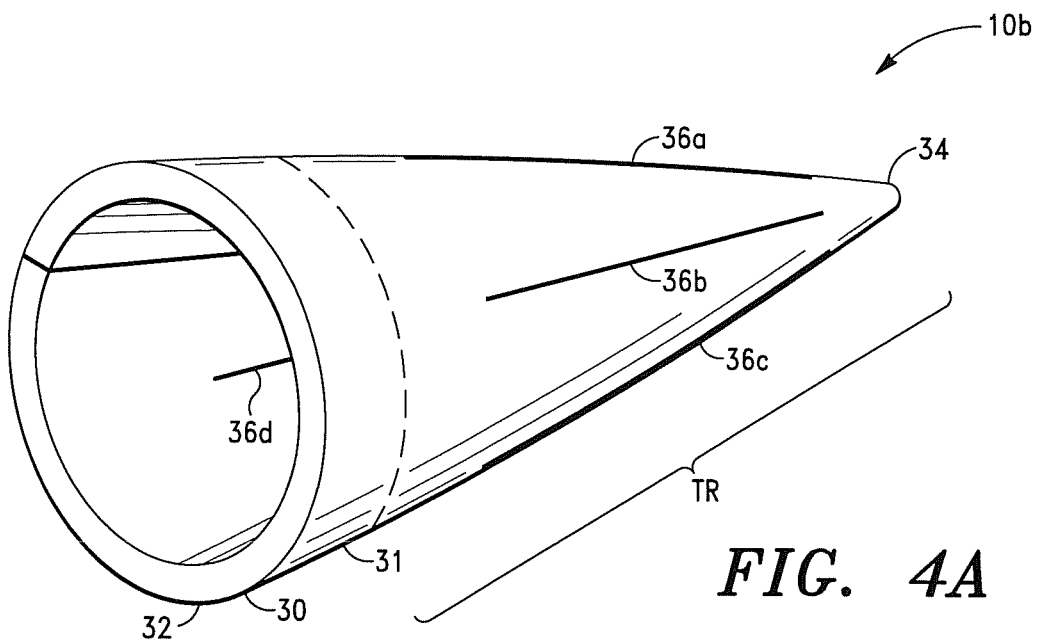
FIG. 4A is a perspective view of one embodiment of a base "sheet structure" valve structure, in accordance with the invention.
Figure 4B:
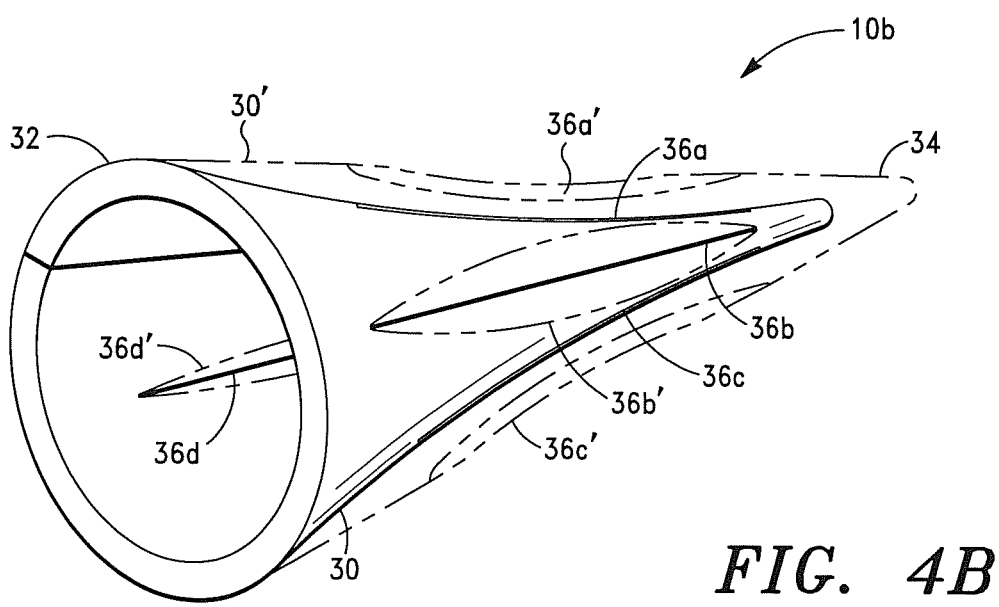
FIG. 4B is a further perspective view of the base "sheet structure" valve structure shown in FIG. 4A, in accordance with the invention.
Figure 4C:
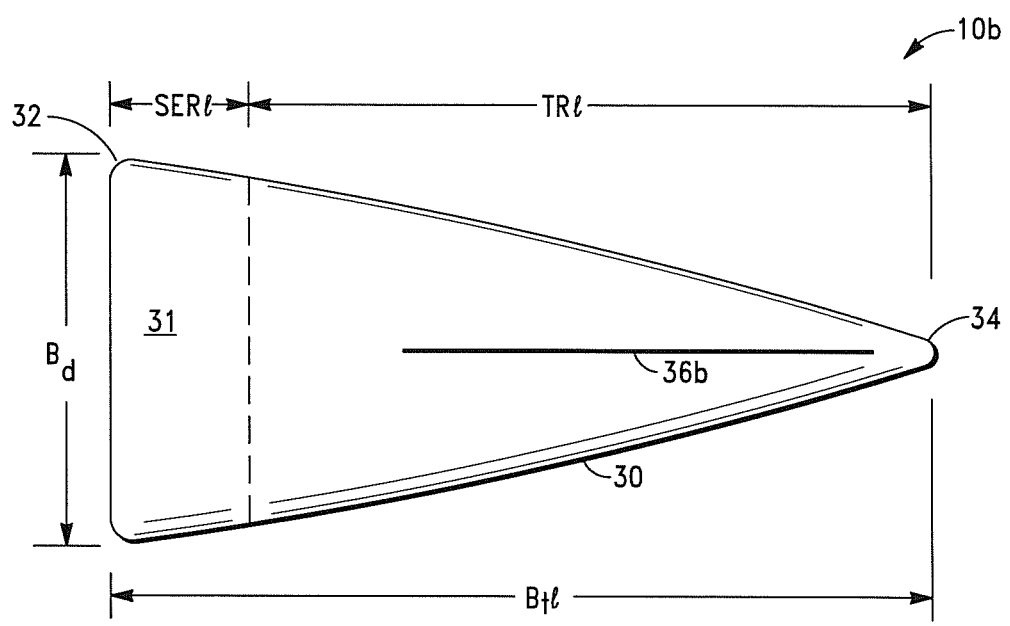
FIG. 4C is a side plan view of the base "sheet structure" valve structure shown in FIG. 4A, in accordance with the invention.

Referring now to FIGS. 4A-4C, there is shown another embodiment of a base valve structure of the invention, denoted 10b.

As set also forth in Applicant's U.S. Pat. Nos. 10,188,509 and 10,188,510, and illustrated in FIGS. 4A and 4B, the base valve structure 10b preferably comprises a base sheet member 30 comprising a proximal valve annulus engagement end 32 and distal end 34, and a plurality of flow modulation means, i.e., open regions or interstices, 36a-36d that are preferably disposed linearly over a portion of the length of the base sheet member 30.

Preferably, the distal ends of the interstices 36a-36d are disposed proximate the distal end 34 of the base sheet member 30 and, hence, base valve structure 10b to prevent blood pooling proximate the distal end 34 of the base sheet member 30.

As also set forth in Applicant's U.S. Pat. Nos. 10,188,509 and 10,188,510, when the base sheet member 30 is engaged to a valve annulus, such as a mitral valve annulus, and receives blood flow therein that exhibits a first positive fluid pressure, whereby a first positive pressure differential between first internal valvular pressure (resulting from the first positive fluid pressure) and first external pressure is generated and internal forces are exerted on the internal surface of the base sheet member 30, i.e., taper region thereof (denoted "TR" in FIG. 4A), the base sheet member 30 is similarly adapted to expand (i.e., deflect outwardly) to an expanded configuration, as shown in phantom and denoted 30' in FIG. 4B, and transition from the expanded configuration to a contracted configuration during transition of the first positive pressure differential to a second pressure differential between second internal valvular pressure and second external or left ventricle pressure, the second pressure differential being lower than the first positive pressure differential, such as when the blood within base sheet member 30 exhibits a second positive fluid pressure that is less than the first positive fluid pressure, i.e., a reduced positive fluid pressure or a negative fluid pressure.

As further set forth in Applicant's U.S. Pat. Nos. 10,188,509 and 10,188,510, the interstices 36a-36d are configured and adapted to open to an open or unrestricted configuration during the noted expansion of the base sheet member 30' (denoted 36a', 36b', 36c' and 36d'), wherein the blood is allowed to be transmitted through the interstices 36a', 36b', 36c', 36d' and out of the base sheet member 30', and transition from the open or unrestricted configuration to a restricted or closed configuration during the noted transition of the base sheet member 30' from the expanded configuration to the contracted configuration 30, wherein the blood through and out of the base sheet member 30 is restricted.

According to the invention, the base valve structure 10b shown in FIGS. 4A-4C and described above can similarly be employed to construct the prosthetic AV valves of the invention, including, without limitation, prosthetic "mitral" tissue valves and prosthetic "tricuspid" tissue valves. The dimensions of which are similarly dependent on various factors, such as the specific application, and the gender, age and cardiac pathologies of the subject.

Referring now to FIG. 4C, for purposes of similarly describing the dimensional relationships by and between the base valve structure 10b and internal stent structures of the invention, the seminal dimensions of the base valve structure 10b are similarly defined as follows:

$B_v l$ represents the total length of the base valve structure 10b;

TRl represents the length of the flow modulating taper region (TR) of the base valve structure 10b; and $B_d$ represents the operative diameter of the proximal valve annulus engagement end (32) of the base valve structure 10b.

As illustrated in FIG. 4A, to facilitate engagement of the stent structures of the invention to the base valve structure 10b, in a preferred embodiment, the base valve structure 10b comprises a stent engagement region 31, i.e., an extended proximal valve annulus engagement end and, thereby, an extended valve structure length ($B_v l$). As illustrated in FIG. 4C, the length of the stent engagement end 31 is represented by SERC.

As indicated above, in a preferred embodiment of the invention, the prosthetic valves of the invention further comprise an expandable stent structure that is adapted to (i) enhance the structural integrity of the prosthetic valves, (ii) position the prosthetic valves at a desired valve annulus region, and, in some embodiments, (iii) secure the prosthetic valve to the valve annulus region.

Figure 5A:
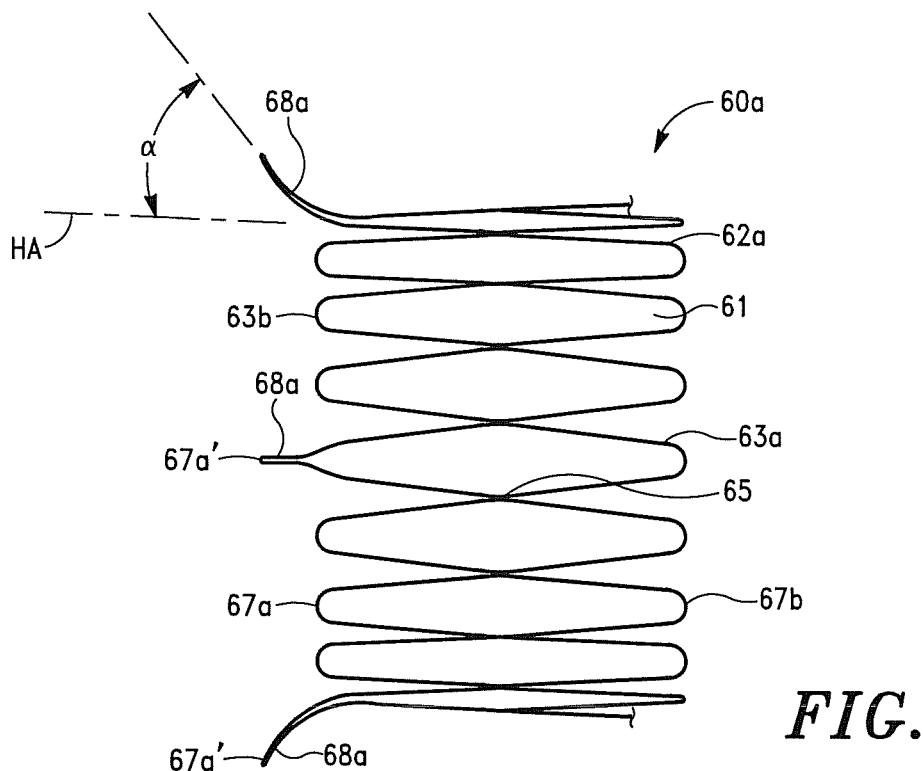
FIG. 5A is a partial side plan view of one embodiment of an expandable stent structure, in accordance with the invention.

Referring now to FIG. 5A, one embodiment of an expandable stent structure of the invention will be described in detail.

As illustrated in FIG. 5A, the expandable stent structure 60a comprises a cross-linked wire structure 62a comprising two (2) band elements 63a, 63b that form a substantially tubular configuration comprising a plurality of substantially uniform rhombus shaped interconnecting cells 61 having proximal and distal ends 67a, 67b.

As additionally illustrated in FIG. 5A, in a preferred embodiment, the interconnecting cells 61 are in communication at points 65.

Figure 12:
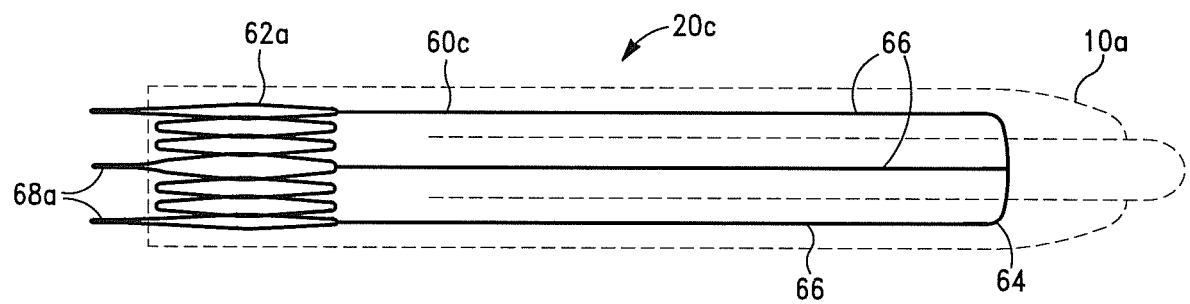
FIG. 12 is a side plan view of the prosthetic valve shown in FIG. 8A in a compressed pre-deployment configuration, in accordance with the invention.
Figure 13:
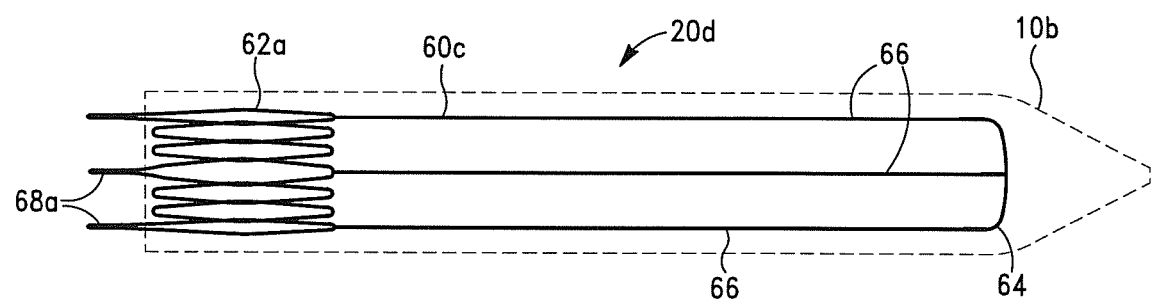
FIG. 13 is a side plan view of the prosthetic valve shown in FIG. 10A in a compressed pre-deployment configuration, in accordance with the invention.

In a preferred embodiment of the invention, the cross-linked wire structure 62a (and cross-linked wire structure 62b, discussed below) is adapted to be compressed to a reduced size (i.e., diameter) tubular configuration and transition from the reduced size tubular configuration to an expanded post-deployment configuration (via stent material properties or an internal radial force), such as shown in FIGS. 12 and 13.

According to the invention, the interconnecting cells 61 can comprise various alternative shapes, such as, without limitation, an ellipse shape; provided, however, that the shape allows the cross-linked wire structure 62a (and cross-linked wire structure 62b) to be compressed to a reduced size (i.e., diameter) tubular configuration and transition from the reduced size tubular configuration to an expanded post-deployment configuration.

According to the invention, the cross-linked wire structure 62a (and cross-linked wire structure 62b) can also comprise various additional suitable single and multiple wire stent structure configurations, including, without limitation, a "Z-stent" design, Gianturco stent design, Gianturco-Roubin stent design and undulating stent design. Further suitable stent structure configurations are disclosed in Applicant's U.S. application Ser. No. 14/958,034, which is incorporated by reference herein.

As further illustrated in FIG. 5A, in a preferred embodiment, the expandable stent structure 60a further comprises a plurality of positioning and anchoring tethers 68a.

According to the invention, the tethers 68a are positioned, configured and adapted to pierce cardiovascular tissue and, thereby, position the expandable stent structure 60a (and hence, prosthetic valve formed therewith) at a desired valve annulus region and, in some embodiments, secure the prosthetic valve thereto during delivery of the prosthetic valve to the valve annulus region.

As illustrated in FIG. 5A, in a preferred embodiment, the tethers 68a comprise extended, angled proximal ends 67a of the interconnecting cells 61.

As further illustrated in FIG. 5A, in a preferred embodiment, the tethers 68a extend proximally from the expandable stent structure 60a to, as indicated above, position a prosthetic valve of the invention formed therewith at a desired valve annulus region and secure the prosthetic valve thereto during delivery of the prosthetic valve to the valve annulus region.

According to the invention, the tethers 68a (and tethers 68b, discussed below) can extend proximally from the stent structure 60a at various angles. In a preferred embodiment, the tethers 68a extend proximally from the stent structure 60a at an angle α relative to the horizontal side plane axis (denoted "HA" in FIG. 5A) in the range of 5° to 45°.

In a preferred embodiment, the tethers 68a (and tethers 68b) comprise a pointed end region 67a' to facilitate piercing and engagement of tissue.

In a preferred embodiment, the tethers 68a are positioned circumferentially and, preferably, equally spaced on the cross-linked wire structure 62a.

Figure 5B:
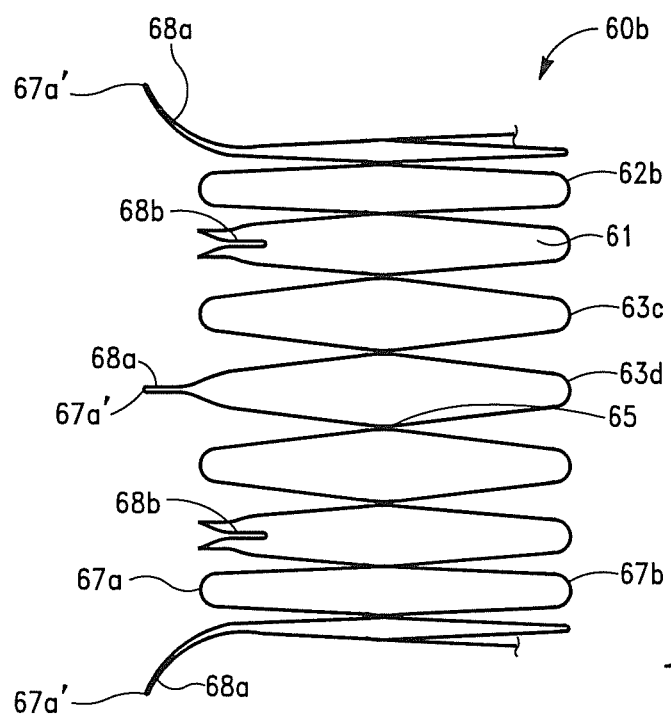
FIG. 5B is a partial side plan view of another embodiment of an expandable stent structure, in accordance with the invention.

Referring now to FIG. 5B, there is shown another embodiment of an expandable stent structure of the invention.

As illustrated in FIG. 5B, the expandable stent structure 60b similarly comprises a cross-linked wire structure (in this embodiment, denoted "62b") comprising two (2) band elements 63c, 63d, which similarly form a substantially tubular configuration comprising a plurality of substantially uniform rhombus shaped interconnecting cells 61 having proximal and distal ends 67a, 67b.

Figure 9:
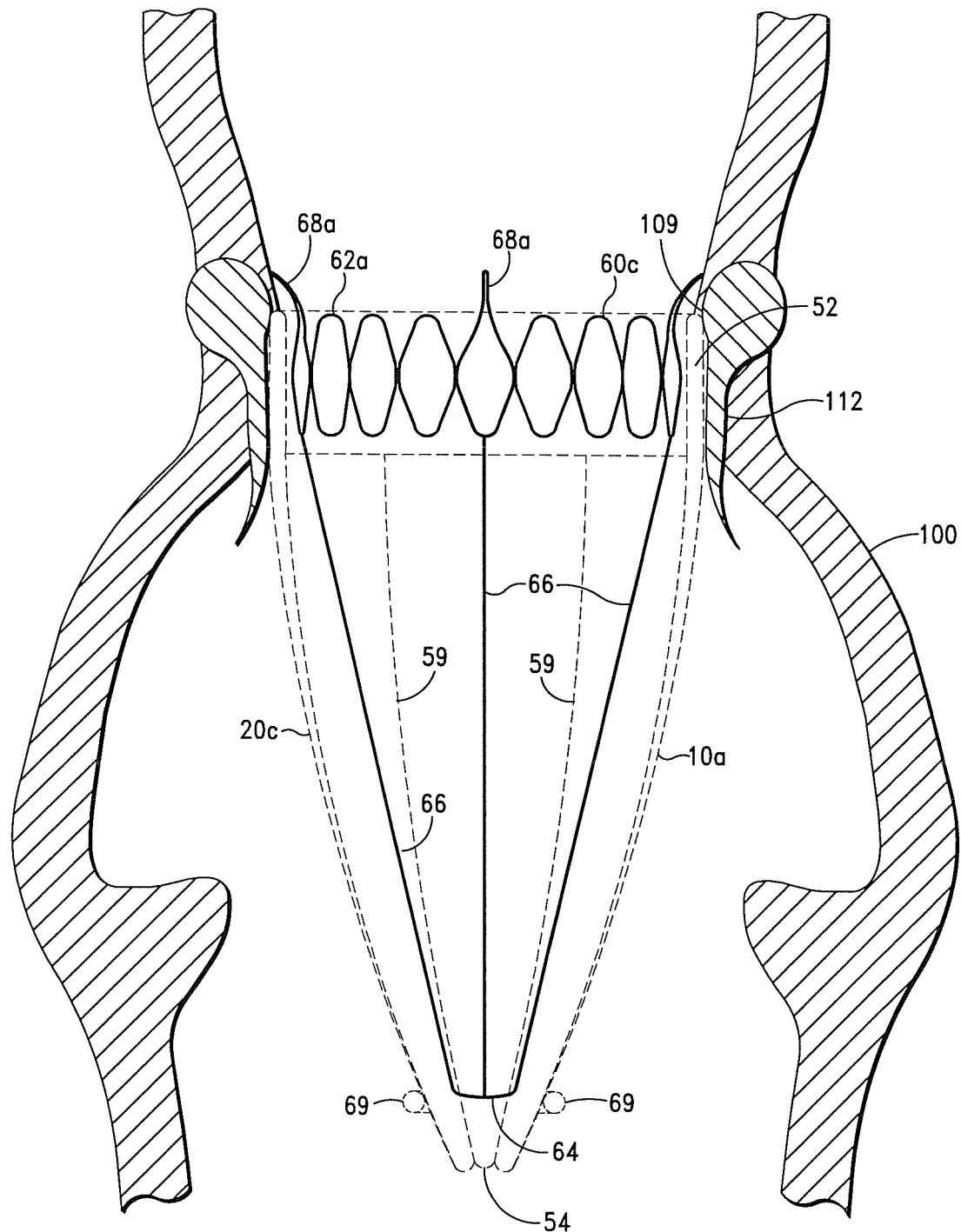
FIG. 9 is a side plan view of the prosthetic valve shown in FIG. 8A engaged to a tricuspid valve annulus, in accordance with the invention.
Figure 11:
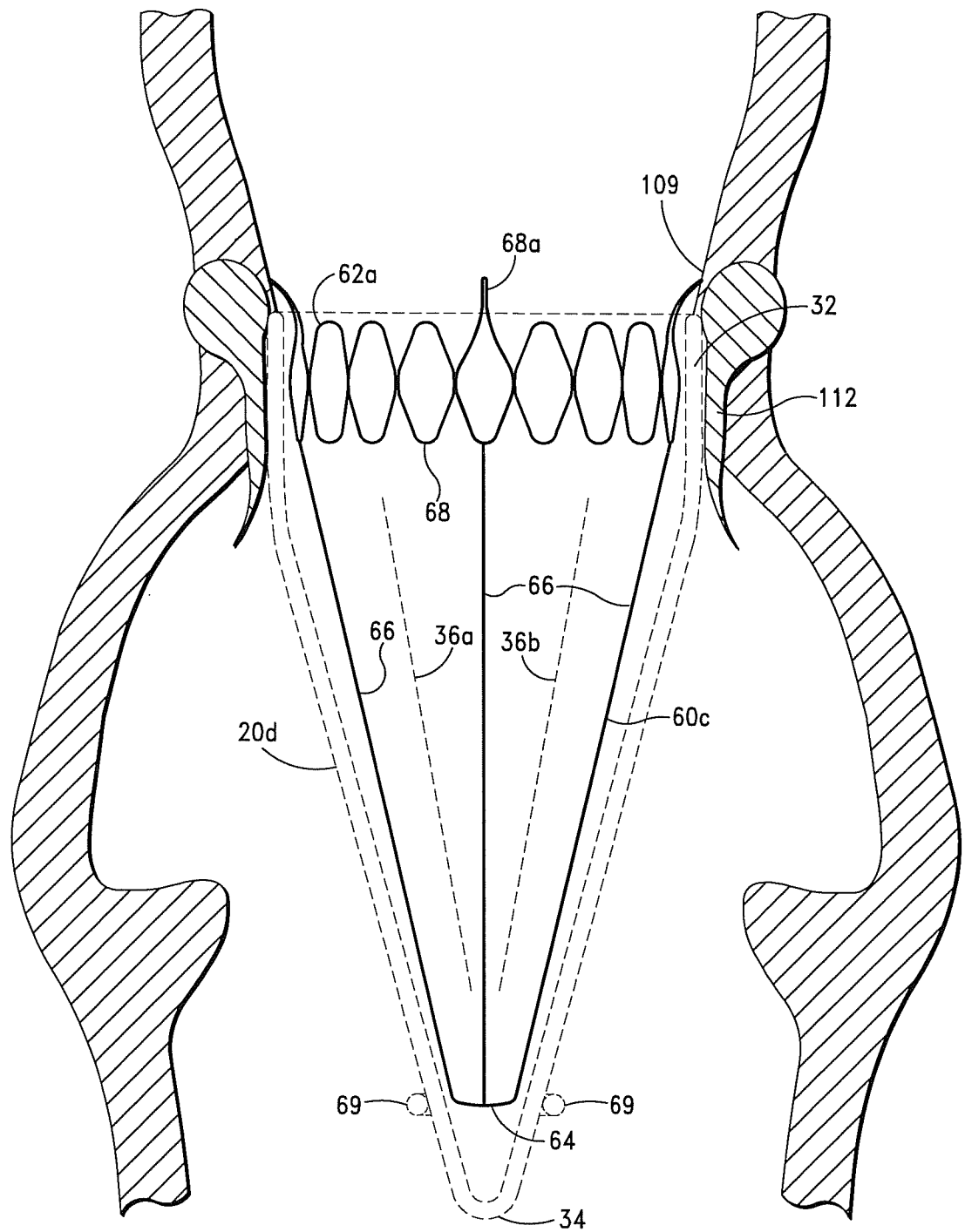
FIG. 11 is a side plan view of the prosthetic valve shown in FIG. 10A engaged to a tricuspid valve annulus, in accordance with the invention.
Figure 14:
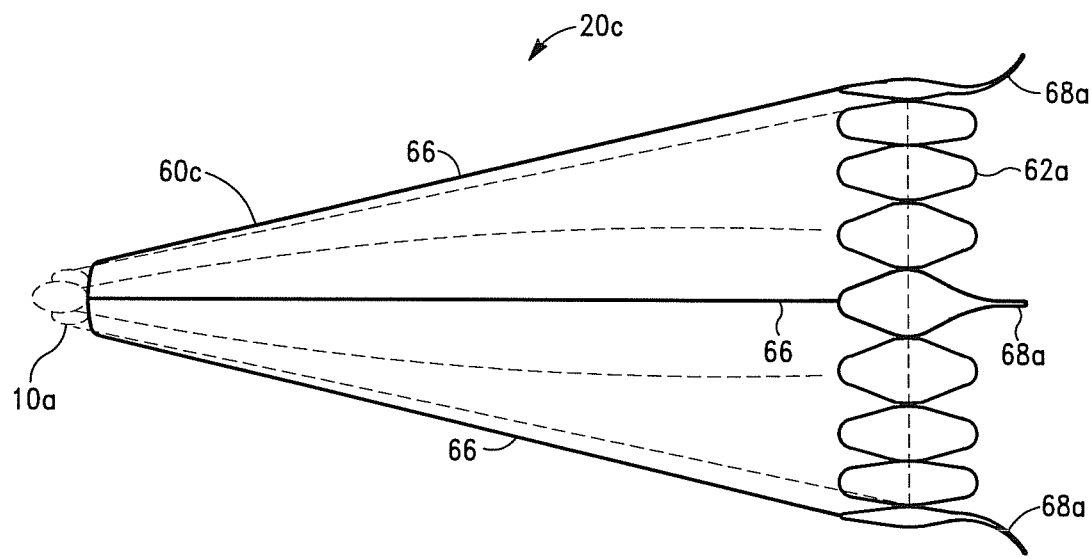
FIG. 14 is a perspective view of the prosthetic valve shown in FIG. 8A in an everted pre-deployment configuration, in accordance with the invention.
Figure 15:
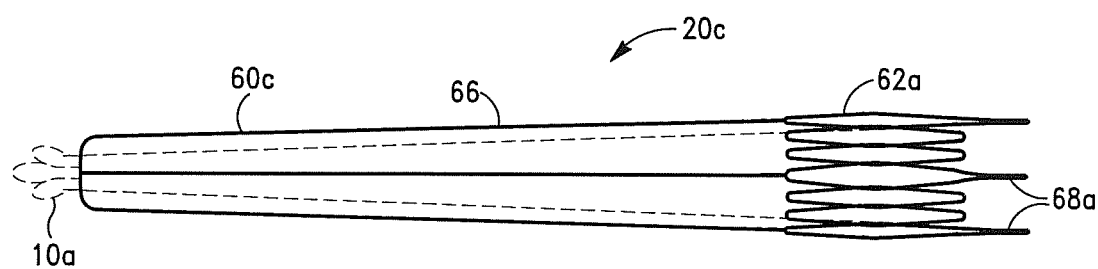
FIG. 15 is a perspective view of the prosthetic valve shown in FIG. 14 in an everted, compressed pre-deployment configuration, in accordance with the invention.

However, as illustrated in FIG. 5B, in this embodiment, the expandable stent structure 60b further comprises positioning and anchoring tethers that alternate in opposing directions, i.e., tethers 68a that extend proximally and tethers 68b that extend distally, to position prosthetic valves of the invention formed therewith at a desired valve annulus region and secure the prosthetic valves thereto during delivery of the prosthetic valves to the valve annulus region in an operative configuration and direction, as shown in FIGS. 9 and 11, and an everted configuration and direction, as shown in FIGS. 14 and 15 and discussed below.

Figure 6A:
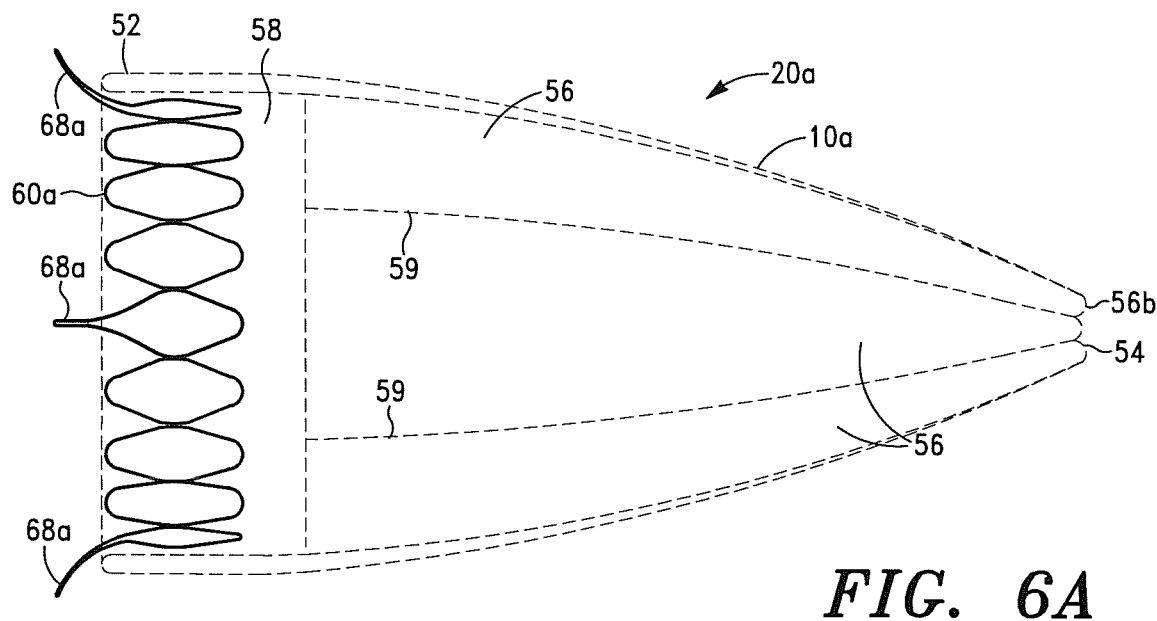
FIG. 6A is a side plan partial sectional view of one embodiment of a prosthetic valve comprising the base valve structure shown in FIG. 3A and the stent structure shown in FIG. 5A, in accordance with the invention.
Figure 6B:
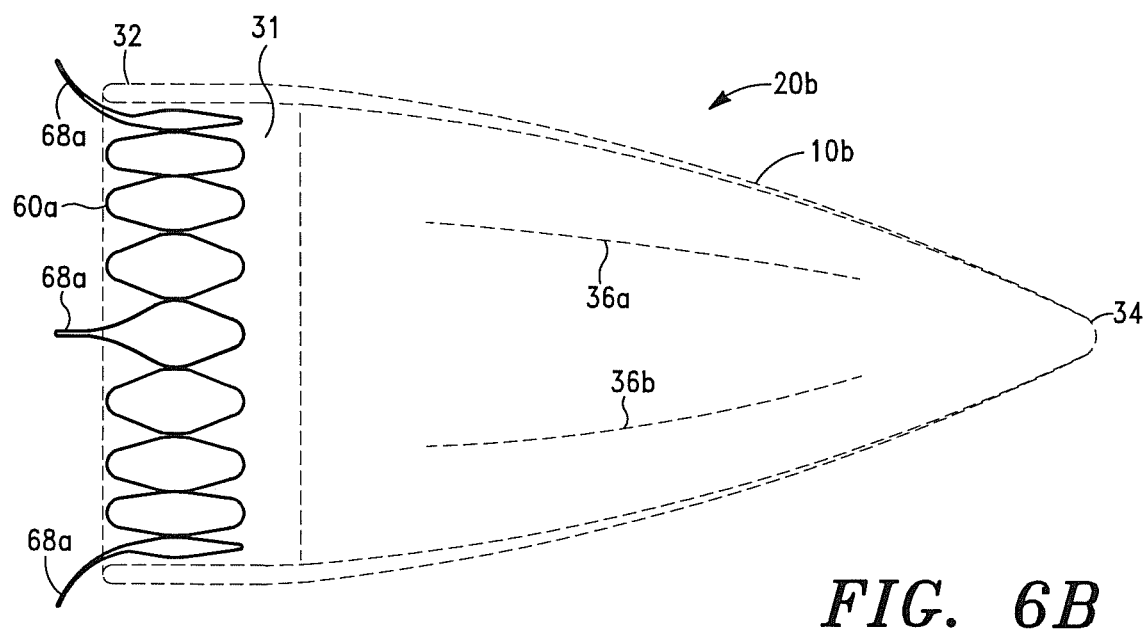
FIG. 6B is a side plan partial sectional view of another embodiment of a prosthetic valve comprising the base valve structure shown in FIG. 4A and the stent structure shown in FIG. 5A, in accordance with the invention.

Referring now to FIGS. 6A and 6B, there are shown illustrations of prosthetic valves of the invention comprising base valve structure 10a and expandable stent structure 60a, i.e., prosthetic valve 20a, (FIG. 6A) and base valve structure 10b and expandable stent structure 60a, i.e., prosthetic valve 20b (FIG. 6B).

As illustrated in FIGS. 6A and 6B, in a preferred embodiment, the expandable stent structure 60a is disposed proximate the proximal valve annulus engagement ends 52, 32 of base valve structures 10a and 10b, respectively.

According to the invention, the expandable stent structure 60a (and expandable stent structure 60b) can be secured to the proximal valve annulus engagement ends 52, 32 of base valve structures 10a and 10b by various conventional means.

In some embodiments of the invention, the expandable stent structure 60a (and expandable stent structure 60b) is secured to the proximal valve annulus engagement ends 52, 32 of base valve structures 10a and 10b, respectively, by bonding the expandable stent structure 60a (and expandable stent structure 60b) thereto with a conventional adhesive.

According to the invention, suitable adhesives include, without limitation, synthetic polymer glues including, without limitation, epoxy resins, epoxy putty, ethylene-vinyl acetate, phenol formaldehyde resins, polyamides, polyester resins, polypropylene, polysulfides, polyurethane, polyvinyl acetate, polyvinyl alcohol, polyvinyl chloride, polyvinylpyrrolidone, silicones and styrene acrylic copolymer; synthetic monomer glues, including, without limitation, acrylnitrile, cyanoacrylate, acrylic and resorcinol glue; and solvent-type glues, including, without limitation, polystyrene cement/butanone and dichloromethane.

In some embodiments of the invention, the expandable stent structure 60a (and expandable stent structure 60b) is secured to the proximal valve annulus engagement ends 52, 32 of base valve structures 10a and 10b, respectively, by folding the proximal valve annulus engagement ends 52, 32 of base valve structures 10a, 10b inwardly (i.e., in the base valve structure lumen) and securing the proximal valve annulus engagement ends 52, 32 to the inner surface of base valve structures 10a, 10b via sutures.

In a preferred embodiment, the expandable stent structure 60a, i.e., cross-linked wire structure 62a thereof, is sized and configured to accommodate the operative diameter of the proximal valve annulus engagement ends 52, 32 of base valve structures 10a and 10b, respectively (denoted "$B_d$" in FIGS. 3C and 4C).

As discussed in detail below, in a preferred embodiment of the invention, the diameter of the cross-linked wire structure 62a is in the range of 96% to 99% of the operative diameter (Ba) of the proximal valve annulus engagement ends 52, 32 of base valve structures 10a and 10b.

According to the invention, the width of the cross-linked wire structure 62a is preferably in the range of 50% to 90% of the length of the circumferential ribbon connection region 58 and stent engagement region 31 of the base valve structures 10a and 10b (denoted "RCRl" in FIG. 3C and "SERl" in FIG. 4C, respectively).

In a preferred embodiment the invention, the width of the cross-linked wire structure 62a is preferably in the range of 70% to 90% of the length of the circumferential ribbon connection region 58 and stent engagement region 31 of the base valve structures 10a and 10b.

According to the invention, the expandable stent structures 60a, 60b can comprise various biocompatible materials.

In some embodiments, the expandable stent structures 60a, 60b comprise one of the aforementioned polymeric compositions.

In some embodiments, the expandable stent structures 60a, 60b comprise a biocompatible metal, including, without limitation, stainless steel, titanium, magnesium, silver, platinum, palladium, gold, tantalum, iridium, tungsten, cobalt, chromium, cobalt-chromium (e.g., cobalt-chromium alloy 1058), cobalt-based 35N alloy, nickel-based alloy 625, a molybdenum alloy, a molybdenum alloy including about 0.4% to about 0.8% of lanthanum oxide ($La_2O_3$), a nickel-titanium alloy and alloys thereof.

In some embodiments, the expandable stent structures 60a, 60b comprise a shape-memory polymer or ceramic, including, without limitation, polyurethanes with ionic or mesogenic components made by a prepolymer method, a block copolymer of polyethylene terephthalate (PET) and polyethyleneoxide (PEO), block copolymers containing polystyrene and poly(1,4-butadiene), an ABA triblock copolymer made from poly (2-methyl-2-oxazoline) and polytetrahydrofuran, and the ceramic Mn-doped (Pb, Sr) TiO3.

As indicated above, in a preferred embodiment, the expandable stent structures 60a, 60b comprise a shape-memory, surgical-grade metal alloy.

According to the invention, suitable shape-memory alloys include, without limitation, nickel-titanium (Ni—Ti) alloys, Copper (Cu)—Zinc (Zn)—Aluminum (Al)—Nickel (Ni) alloys and Cu—Al—Ni alloys.

In a preferred embodiment, the expandable stent structures 60a, 60b comprise a Ni—Ti alloy, referred to hereinafter as Nitinol®, which, as indicated above, has been drawn or formed into a wire structure.

In a preferred embodiment, the Nitinol® wire structure comprises a diameter in the range of 0.010 in. to 0.015 in.

In a preferred embodiment, the expandable Nitinol® stent structures 60a, 60b comprise superelastic structures, whereby the stent structures 60a, 60b are adapted to undergo a crystal phase transformation from a martensite crystal structure to an austenite crystal structure at a pre-defined transformation temperature and can be deformed (and, hence, shaped) at or above the transformation temperature, stay in the deformed configuration when the force(s) exerted to deform, i.e., shape, the stent structures 60a, 60b has been removed, transition from the austenite crystal structure back to the martensite crystal structure when the stent structures 60a, 60b are cooled below the transformation temperature, and then revert back to the original deformed configuration upon heating the stent structures 60a, 60b above the transformation temperature, e.g., core temperature of a patient.

Figure 7:
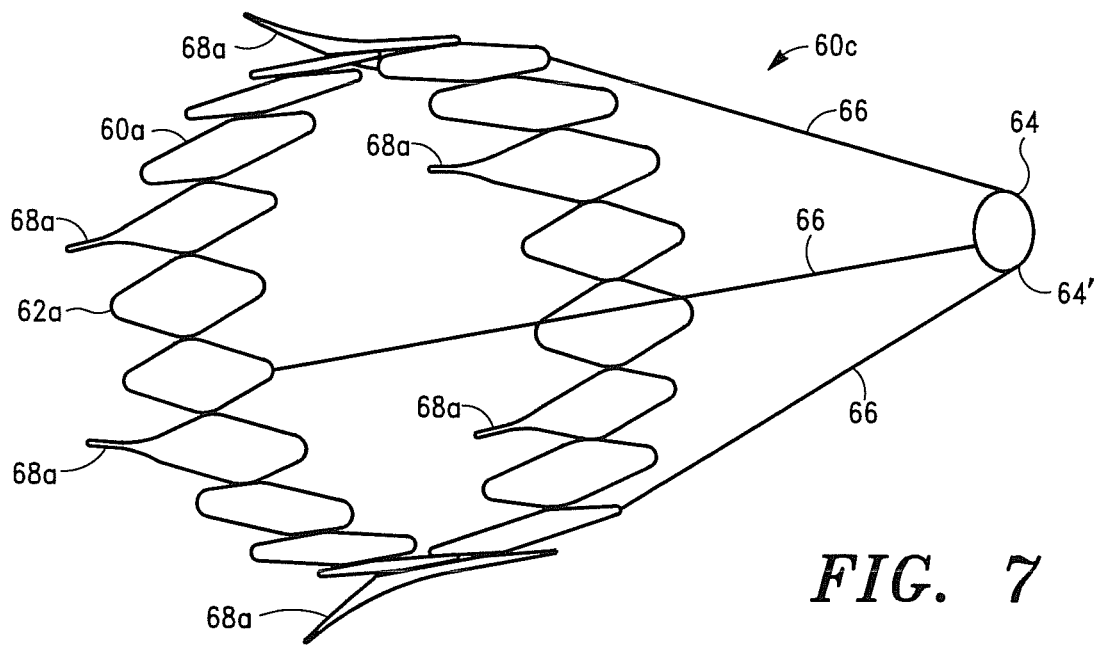
FIG. 7 is a perspective view of another embodiment of an expandable stent structure, in accordance with the invention.

Referring now to FIG. 7, there is shown another embodiment of a stent structure of the invention.

As illustrated in FIG. 7, in one preferred embodiment, the expandable stent structure 60c comprises cross-linked wire structure 62a described above, a circumferential distal end region 64 and a plurality of links 66 disposed between and engaged to the cross-linked wire structure 62a and circumferential distal end region 64, whereby the cross-linked wire structure 62a and circumferential distal end region 64 are in communication.

According to the invention, the expandable stent structure 60c can also comprise cross-linked wire structure 62b described above.

According to the invention, the links 66 can be attached to the cross-linked wire structure 62a and circumferential distal end region 64 by various conventional means. In a preferred embodiment, the links 66 are soldered to the cross-linked wire structure 62a and circumferential distal end region 64.

As further illustrated in FIG. 7, in a preferred embodiment, the circumferential distal end region 64 preferably comprises a solid, toroidal shaped (i.e., doughnut-shaped) structure.

According to the invention, the circumferential distal end region 64 can further comprise a cross-linked wire structure that is similar to cross-linked wire structures 62a, 62b.

Figure 8A:
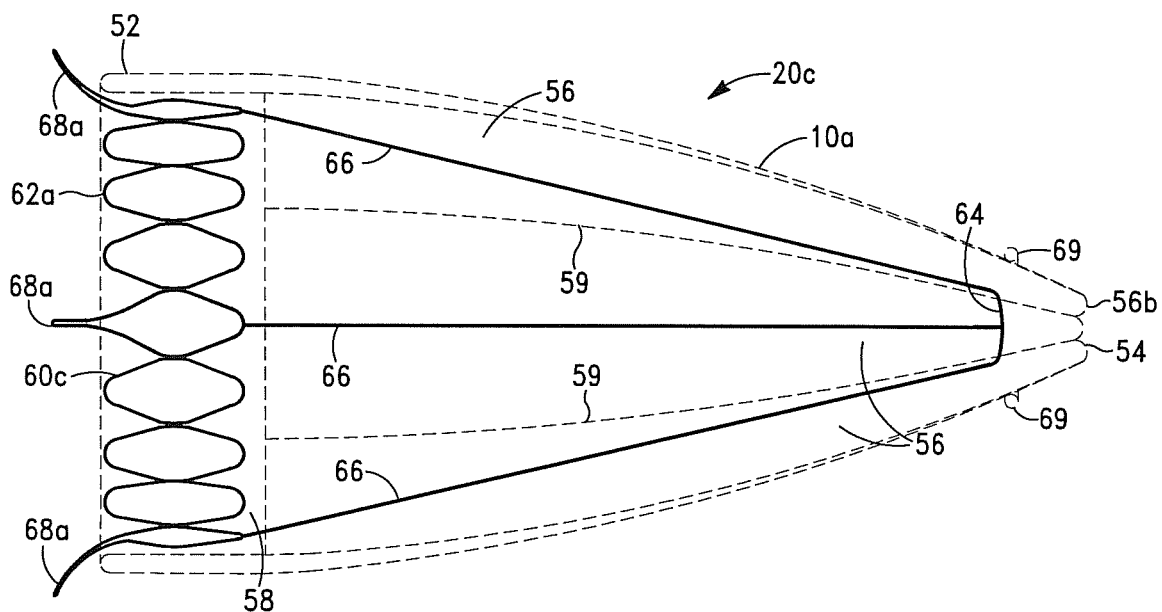
FIG. 8A is a side plan partial sectional view of one embodiment of a prosthetic valve comprising the base valve structure shown in FIG. 3A and the stent structure shown in FIG. 7, in accordance with the invention.

As illustrated in FIGS. 8A and 11, and discussed in detail below, the circumferential distal end region 64 is preferably sized and configured to accommodate positioning at a pre-determined internal distal region of the base valve structures 10a, 10b.

Thus, as illustrated in FIG. 7, as well as FIGS. 8A and 11, the expandable stent structure 60c comprises a tapered configuration to accommodate the taper configurations of the base valve structures 10a, 10b.

As further illustrated in FIG. 7, the expandable stent structure 60c comprises three (3) links 66, which, as indicated above, are disposed between and engaged to the cross-linked wire structure 62a and the circumferential distal end region 64.

In a preferred embodiment, the links 66 similarly comprise a wire structure.

According to the invention, the length of the expandable stent structure 60c (with the links 66 disposed between and engaged to the cross-linked wire structure 62a (and expandable stent structure 62b, if employed) and the circumferential distal end region 64 from the proximal ends 67a of the interconnecting cells 61 of the cross-linked wire structure 62a (or 62b) to the distal end 64' of the circumferential distal end region 64 is preferably in the range of 80% to 95% of the length of base valve structures 10a and 10b (denoted "Btl" in FIGS. 3C and 4C).

According to the invention, the links 66 and circumferential distal end region 64 can similarly comprise various biocompatible materials.

In a preferred embodiment, the links 66 and circumferential distal end region 64 similarly comprise Nitinol®.

Referring now to FIG. 8A, there is shown one embodiment of a prosthetic valve of the invention, denoted 20c, incorporating the base "ribbon structure" valve structure 10a shown in FIGS. 3A and 3B and the expandable stent structure 60c shown in FIG. 7.

As illustrated in FIG. 8A, the cross-linked wire structure 62a of stent structure 60c is preferably disposed proximate the circumferential ribbon connection region 58 of base valve structure 10a.

As indicated above and illustrated in FIG. 8A, the cross-linked wire structure 62a is sized and configured to accommodate the operative diameter ("$B_d$") of the proximal valve annulus engagement end 52 of the base valve structure 10a.

As further indicated above and illustrated in FIG. 8A, the length of the expandable stent structure 60c (with the links 66 disposed between and engaged to the cross-linked wire structure 62a and the circumferential distal end region 64) from the proximal ends 67a of the interconnecting cells 61 of the cross-linked wire structure 62a to the distal end 64' of the circumferential distal end region 64 is in the range of 80% to 95% of the length of base valve structure 10a.

Figure 8B:
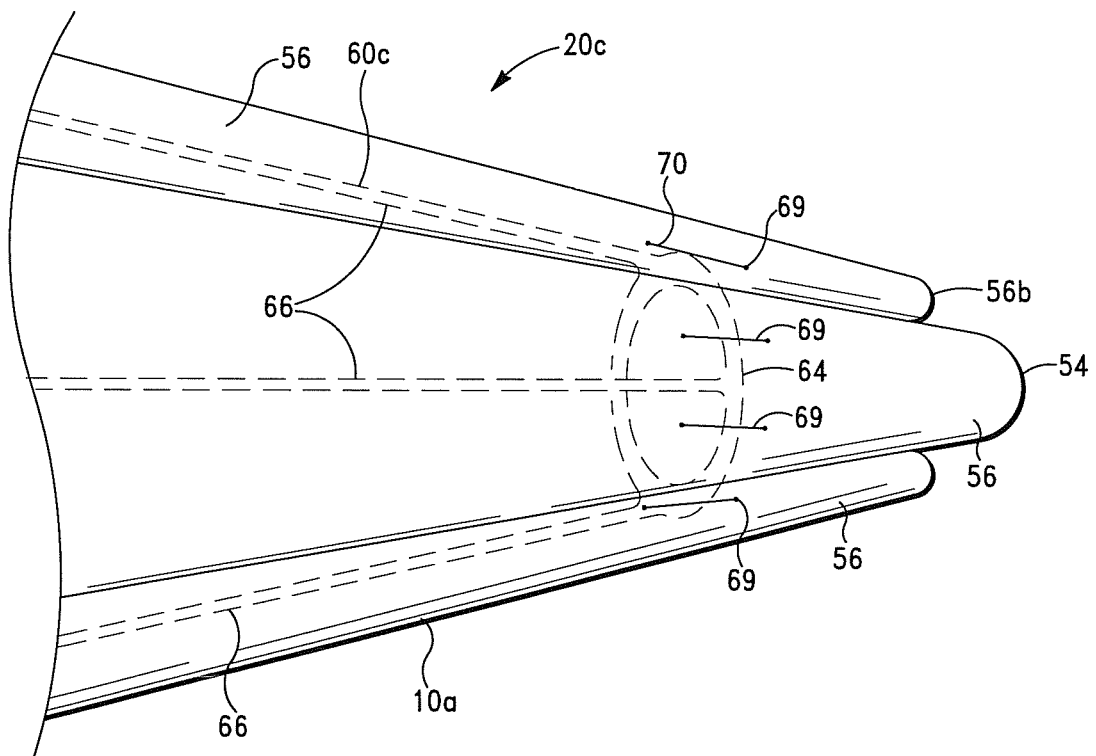
FIGS. 8B and 8C are partial side plan views of the prosthetic valve shown in FIG. 8A showing the distal end of the base valve structure sutured to the circumferential distal end region of the stent structure, in accordance with the invention.

Referring now to FIG. 8B, the distal ends 56b of the ribbons 56 of base valve structure 10a (and, hence, distal end 54 of the base valve structure 10a) are preferably secured to the circumferential distal end region 64 of the expandable stent structure 60c at commissural regions 69.

According to the invention, the distal ends 56b of the ribbons 56 of base valve structure 10a (and, hence, distal end 54 of the base valve structure 10a) can be secured to the circumferential distal end region 64 using any conventional means.

Figure 8C:
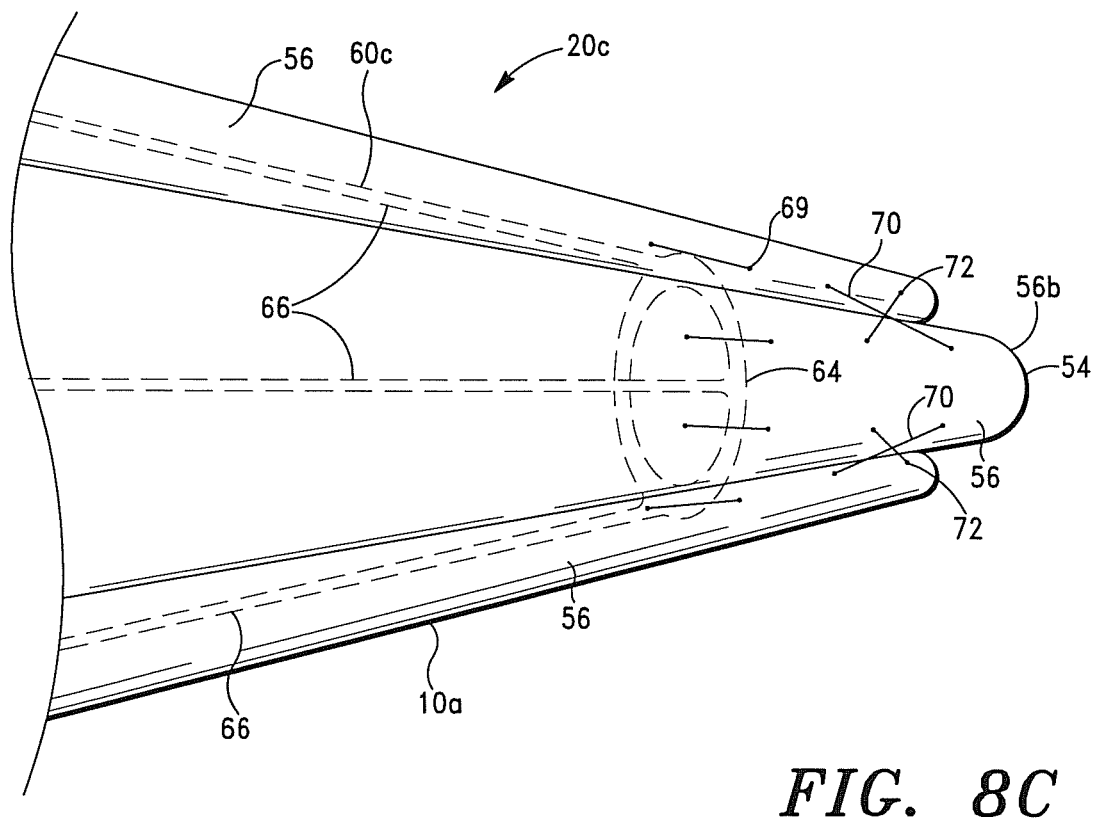

As illustrated in FIGS. 8B and 8C, in a preferred embodiment, the distal ends 56b of the ribbons 56 of base valve structure 10a (and, hence, distal end 54 of the base valve structure 10a) are sutured (via suture 70) to the circumferential distal end region 64 of the expandable stent structure 60c.

As further illustrated in FIG. 8C, to ensure a joined, sealed relationship of the distal ends 56b of the ribbons 56 of base valve structure 10a, whereby blood flow therethrough is restricted, in a preferred embodiment, the distal ends 56b of the ribbons 56 of base valve structure 10a are further sutured at ribbon commissural regions 72.

Referring now to FIG. 9, there is shown prosthetic valve 20c disposed in a tricuspid valve region 109 of a subject's heart 100.

As illustrated in FIG. 9, the cross-linked wire structure 62a of expandable stent structure 60c and, thereby, proximal annulus engagement end 52 of the base valve member 10a is disposed proximate the cardiovascular tissue of the tricuspid valve region 109.

Figure 10A:
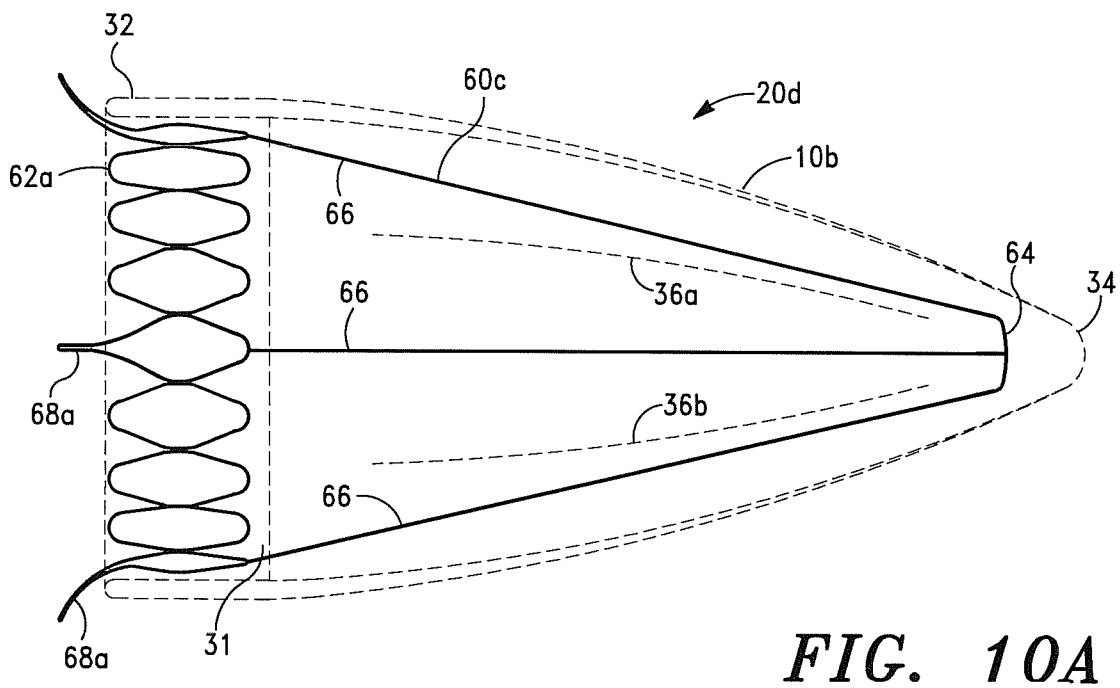
FIG. 10A is a side plan partial sectional view of another embodiment of a prosthetic valve comprising the base valve structure shown in FIG. 4A and the stent structure shown in FIG. 7, in accordance with the invention.

Referring now to FIG. 10A, there is shown one embodiment of a prosthetic valve of the invention, denoted 20d, incorporating the base "sheet structure" valve structure 10b shown in FIGS. 4A and 4B and the expandable stent structure 60c shown in FIG. 7.

As illustrated in FIG. 10A, the cross-linked wire structure 62a of expandable stent structure 60c is similarly disposed proximate the stent engagement region 31 of base valve structure 10b.

As indicated above and illustrated in FIG. 10A, the width of the cross-linked wire structure 62a is similarly in the range of 50% to 90% of the length of the stent engagement region 31 of the base valve structure 10b.

As also indicated above and illustrated in FIG. 10A, the cross-linked wire structure 62a is similarly sized and configured to accommodate the operative diameter ("$B_d$") of the proximal valve annulus engagement end 32 of the base valve structure 10b.

Figure 10B:
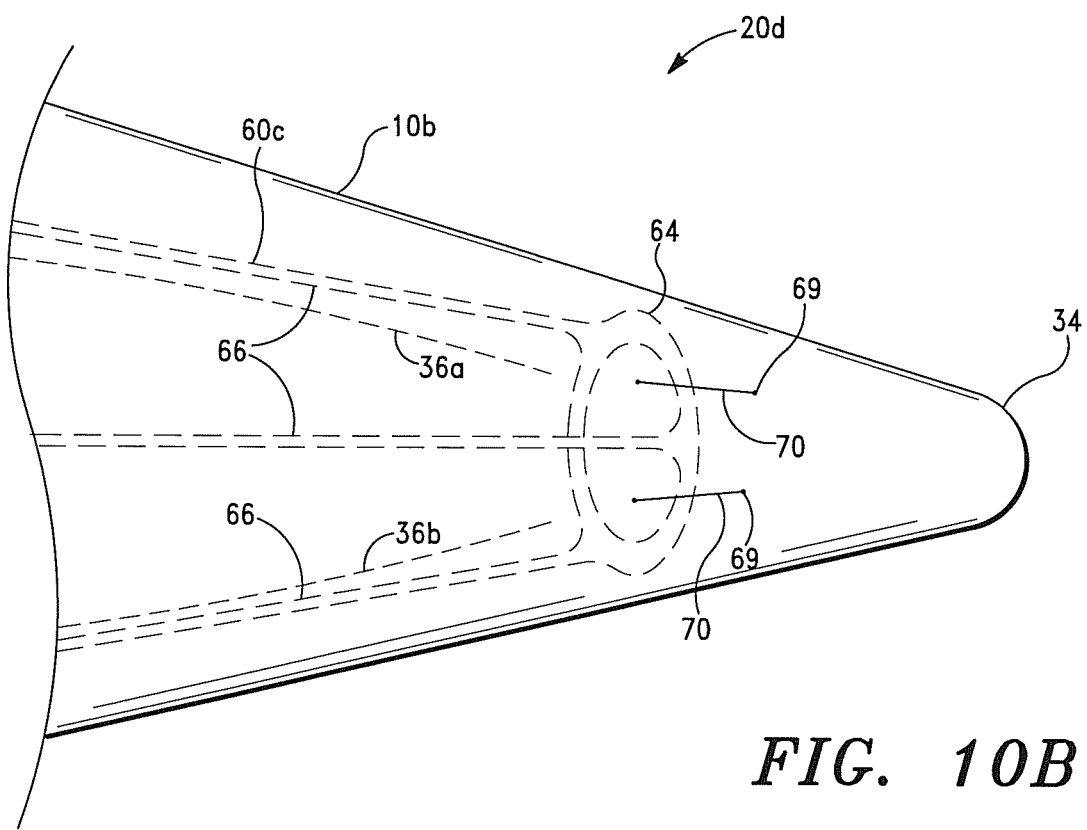
FIG. 10B is a partial side view of the prosthetic valve shown in FIG. 10A showing the distal end of the base valve structure sutured to the circumferential distal end region of the stent structure, in accordance with the invention.

Referring now to FIG. 10B, the distal end 34 of the base valve structure 10b is similarly preferably secured to the circumferential distal end region 64 of the expandable stent structure 60c at commissural regions 69.

According to the invention, the distal end 34 of the base valve structure 10b can be similarly secured to the circumferential distal end region 64 using any conventional means.

As illustrated in FIG. 10B, in a preferred embodiment, the distal end 34 of the base valve structure 10b is sutured (via suture 70) to the circumferential distal end region 64 of the stent structure 60c.

Referring now to FIG. 11, there is shown prosthetic valve 20d disposed in a tricuspid valve region 109 of a subject's heart 100, wherein the cross-linked wire structure 62a of the expandable stent structure 60c and, thereby, proximal annulus engagement end 32 of the base valve member 10b is similarly disposed proximate the cardiovascular tissue of the tricuspid valve region 109.

According to the invention, the prosthetic valves 20a-20d can be implanted in the heart of a patient or subject using any conventional surgical technique.

As illustrated in FIGS. 9 and 11, an additional advantage of the prosthetic valves of the invention is that they can be implanted in a subject without removing the native valve, e.g., tricuspid valve.

As indicated above, in a preferred embodiment of the invention, the cross-linked wire structures 62a, 62b of stent structures 60a-60c are adapted to be compressed to a reduced size (i.e., diameter) tubular configuration, such as shown in FIGS. 12 and 13, to facilitate placement in and slidable translation through a percutaneous valve delivery apparatus or catheter assembly and, thereby, delivered therewith to a valve annulus, and transition from the reduced size tubular configuration to an expanded post-deployment configuration, such as shown in FIGS. 9 and 11.

A further seminal feature of the prosthetic valves 20c, 20d is that the valves 20c, 20d are further configured and adapted to (i) evert to an everted configuration, as illustrated by the everted configuration of prosthetic valve 20c shown in FIG. 14, and (ii) compress to a pre-deployment reduced size tubular configuration when in the everted configuration, as illustrated by the everted reduced size tubular configuration of prosthetic valve 20c shown in FIG. 15, to similarly facilitate placement in and translation through a percutaneous valve delivery apparatus or catheter assembly and, thereby, delivery therewith to a valve annulus, as described in detail in Applicant's U.S. application Ser. No. 17/234,266, filed on Apr. 19, 2021.

In a preferred embodiment, the prosthetic valves 20a-20d are adapted to compress to a pre-deployment everted reduced size tubular configuration diameter in the range of 4-30 French.

As indicated above and will readily be appreciated by one having ordinary skill in the art, the prosthetic valves of the invention provide numerous advantages over prior art prosthetic heart valves. Among the advantages are the following:

The provision of prosthetic valves having stent structures that provide acceptable structural integrity and facilitate percutaneous valve implant procedures to position the prosthetic valves formed therewith in valve annuli;

The provision of prosthetic valves having stent structures that provide acceptable structural integrity and facilitate secure, sealed engagement of the prosthetic valves via percutaneous valve implant procedures;

The provision of prosthetic valves that are configured and adapted to be compressed to a reduced size tubular configuration to facilitate placement in and translation through a percutaneous valve delivery apparatus or catheter assembly and, thereby, delivered therewith to a valve annulus; and The provision of prosthetic valves that are configured and adapted to (i) evert to an everted configuration and (ii) compress to a pre-deployment reduced size tubular configuration when in the everted configuration to facilitate placement in and translation through a percutaneous valve delivery apparatus or catheter assembly and, thereby, delivery therewith to a valve annulus.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A prosthetic valve for modulating fluid flow through a cardiovascular structure during cardiac cycles of a heart, comprising:
 a base valve structure and an expandable stent structure,
 said base valve structure comprising collagenous tissue derived from a first mammalian tissue source,
 said base valve structure further comprising an internal region, an open proximal valve annulus engagement end and a distal valve structure end, said open proximal valve annulus engagement end being configured and adapted to engage a heart valve annulus, receive said fluid flow therein and direct said fluid flow into said internal region of said base valve structure,
 said base valve structure further comprising a plurality of elongated ribbon members that extend from said open proximal valve annulus engagement end to said distal valve structure end, each of said plurality of elongated ribbon members comprising first and second edge regions and proximal and distal ends, said plurality of elongated ribbon members being positioned circumferentially about said base valve structure, wherein said first edge regions of said plurality of elongated ribbon members are positioned proximate said second edge regions of said plurality of elongated ribbon members and form a plurality of flow modulating regions,
 said distal ends of said plurality of elongated ribbon members being positioned proximate each other in a constrained relationship, wherein said fluid flow through said distal ends of said plurality of elongated ribbon members and, thereby, said base valve structure is restricted,
 said plurality of elongated ribbon members being configured and adapted to deflect outwardly when said open proximal valve annulus engagement end of said base valve structure directs said fluid flow into said internal region of said base valve structure and said fluid flow comprises a positive fluid pressure, whereby a first pressure differential between first valvular pressure in said internal region of said base valve structure relative to first external pressure exerted on said base valve structure is generated, wherein each of said plurality of flow modulating regions transitions from a restricted fluid flow configuration to an open fluid flow configuration and allows said fluid flow to be transmitted through said plurality of flow modulating regions and, thereby, through and out of said base valve structure,
 said plurality of elongated ribbon members being further configured and adapted to deflect inwardly when said first pressure differential transitions to a second pressure differential between second valvular pressure in said internal region of said base valve structure relative to second external pressure exerted on said base valve structure, said second pressure differential being lower than said first pressure differential, wherein each of said plurality of flow modulating regions transitions from said open fluid flow configuration to said restricted fluid flow configuration and restricts said fluid flow through said plurality of flow modulating regions and, thereby, through and out of said base valve structure,
 said expandable stent structure being positioned in said internal region of said base valve structure,
 said expandable stent structure comprising a plurality of tethers adapted to pierce cardiovascular tissue and, thereby, position said base valve structure on said heart valve annulus,
 wherein said stent structure comprises a shape-memory alloy, and
 wherein said prosthetic valve is adapted to evert to an everted configuration.

2. The prosthetic valve of claim 1, wherein said first mammalian tissue source is selected from the group consisting of the heart, small intestine, large intestine, stomach, lung, liver, kidney, pancreas, peritoneum, placenta, amniotic membrane, umbilical cord, bladder, prostate, and fetal tissue from any mammalian organ.

3. The prosthetic valve of claim 1, wherein said first mammalian tissue source is devoid of xenogeneic antigens.

4. The prosthetic valve of claim 1, wherein said collagenous tissue comprises a first pharmacological agent.

5. The prosthetic valve of claim 4, wherein said first pharmacological agent is selected from the group consisting of an antibiotic, anti-viral agent, analgesic, anti-inflammatory, anti-neoplastic, anti-spasmodic, and anticoagulant and antithrombotic.

6. The prosthetic valve of claim 5, wherein said antibiotic is selected from the group consisting of aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

7. The prosthetic valve of claim 5, wherein said anti-inflammatory is selected from the group consisting of dexamethasone, betamethasone and prednisolone.

8. The prosthetic valve of claim 1, wherein said shape-memory alloy comprises a nickel-titanium (Ni—Ti) alloy.

9. The prosthetic valve of claim 1, wherein said prosthetic valve is further adapted to compress to a pre-deployment reduced size tubular configuration when in said everted configuration, whereby said prosthetic valve can be placed in and slidably translated through a percutaneous valve delivery apparatus and, thereby, delivered therewith to said heart valve annulus.

10. The prosthetic valve of claim 1, wherein said stent structure comprises an outer coating.

11. The prosthetic valve of claim 10, wherein said outer coating comprises an immunomodulating compound.

12. The prosthetic valve of claim 11, wherein said immunomodulating compound comprises a polysaccharide selected from the group consisting of a glycosaminoglycan, dextran, alginate and chitosan.

13. The prosthetic valve of claim 11, wherein said immunomodulating compound comprises a high molecular weight hyaluronic acid (HMW-HA).

14. The prosthetic valve of claim 10, wherein said outer coating comprises an extracellular matrix (ECM) composition comprising acellular ECM derived from a second mammalian tissue source.

15. The prosthetic valve of claim 14, wherein said second mammalian tissue source is selected from the group consisting of small intestine submucosa (SIS), urinary bladder submucosa (UBS), stomach submucosa (SS), heart tissue, mesothelial tissue, placental tissue and omentum tissue.

16. The prosthetic valve of claim 14, wherein said ECM composition is in the form of an expandable composition.

17. The prosthetic valve of claim 10, wherein said outer coating comprises a second pharmacological agent selected from the group consisting of desoximetasone, sirolimus, cyclosporine and prednisolone.

* * * * *